United States Patent
Aviv et al.

(10) Patent No.: US 9,610,353 B2
(45) Date of Patent: *Apr. 4, 2017

(54) MALLEABLE HYDROGEL HYBRIDS MADE OF SELF-ASSEMBLED PEPTIDES AND BIOCOMPATIBLE POLYMERS AND USES THEREOF

(71) Applicant: Technology Innovation Momentum Fund (Israel) Limited Partnership, Tel-Aviv (IL)

(72) Inventors: Moran Aviv, Rishon-LeZion (IL); Ludmila Buzhansky, Ariel (IL); Shmuel Einav, Herzlia (IL); Zvi Nevo, Herzlia (IL); Ehud Gazit, Ramat-HaSharon (IL); Lihi Adler-Abramovich, Herzlia (IL)

(73) Assignee: Technology Innovation Momentum Fund (Israel) Limited Partnership, Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/791,542

(22) Filed: Jul. 6, 2015

(65) Prior Publication Data

US 2015/0306229 A1 Oct. 29, 2015

Related U.S. Application Data

(63) Continuation of application No. 13/701,558, filed as application No. PCT/IL2011/000435 on Jun. 2, 2011, now Pat. No. 9,074,095.

(60) Provisional application No. 61/350,978, filed on Jun. 3, 2010.

(51) Int. Cl.

| | | |
|---|---|---|
| A61F 2/00 | (2006.01) | |
| A61K 47/36 | (2006.01) | |
| A61L 27/20 | (2006.01) | |
| A61L 27/22 | (2006.01) | |
| A61L 27/52 | (2006.01) | |
| A61K 8/64 | (2006.01) | |
| A61K 47/26 | (2006.01) | |
| C08L 89/00 | (2006.01) | |
| A61K 8/04 | (2006.01) | |
| A61K 8/73 | (2006.01) | |
| A61K 47/18 | (2017.01) | |
| A61L 27/26 | (2006.01) | |
| A61Q 19/00 | (2006.01) | |
| A61K 9/16 | (2006.01) | |

(52) U.S. Cl.
CPC ............ *A61K 47/36* (2013.01); *A61K 8/042* (2013.01); *A61K 8/64* (2013.01); *A61K 8/735* (2013.01); *A61K 8/736* (2013.01); *A61K 47/183* (2013.01); *A61K 47/26* (2013.01); *A61L 27/20* (2013.01); *A61L 27/227* (2013.01); *A61L 27/26* (2013.01); *A61L 27/52* (2013.01); *A61Q 19/00* (2013.01); *C08L 89/00* (2013.01); *A61K 9/1694* (2013.01); *A61K 2800/10* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 5,665,428 A | 9/1997 | Cha et al. | |
| 2005/0142152 A1* | 6/2005 | Leshchiner | .......... A61K 9/0014 424/400 |
| 2009/0263429 A1* | 10/2009 | Ulijn | ...................... A61K 38/46 424/400 |
| 2013/0079421 A1 | 3/2013 | Aviv | |

FOREIGN PATENT DOCUMENTS

| | | | |
|---|---|---|---|
| IL | WO 2009022339 A1 * | 2/2009 | .......... A61L 27/227 |
| WO | WO 2007/029003 | 3/2007 | |
| WO | WO 2007/043048 | 4/2007 | |
| WO | WO 2009/022339 | 2/2009 | |
| WO | WO 2011/151832 | 12/2011 | |

OTHER PUBLICATIONS

Communication Pursuant to Article 94(3) EPC Dated Oct. 14, 2013 From the European Patent Office Re. Application No. 11730085.5.
International Preliminary Report on Patentability Dated Dec. 13, 2012 From the International Bureau of WIPO Re. Application No. PCT/IL2011/000435.
International Search Report and the Written Opinion Dated Sep. 28, 2011 From the International Searching Authority Re. Application No. PCT/IL2011/000435.
Notice of Allowance Dated Feb. 23, 2015 From the US Patent and Trademark Office Re. U.S. Appl. No. 13/701,558.

(Continued)

*Primary Examiner* — Susan Tran

(57) ABSTRACT

Hybrid hydrogels formed of a plurality of peptides that are capable of self-assembling into a hydrogel in an aqueous solution and a biocompatible polymer that is characterized by high swelling capability, high elasticity and low mechanical strength are disclosed, with exemplary hybrid hydrogels being formed of a plurality of aromatic dipeptides and hyaluronic acid. The hybrid hydrogels are characterized by controllable mechanical and biological properties which can be adjusted by controlling the concentration ratio of the peptides and the polymer, and which average the mechanical and biological properties of the peptides and the polymer. Processes of preparing the hydrogels and uses thereof in pharmaceutical, cosmetic or cosmeceutic applications such as tissue engineering and/or regeneration are further disclosed.

23 Claims, 12 Drawing Sheets
(11 of 12 Drawing Sheet(s) Filed in Color)

(56) References Cited

OTHER PUBLICATIONS

Official Action Dated Sep. 9, 2014 From the US Patent and Trademark Office Re. U.S. Appl. No. 13/701,558.
Restriction Official Action Dated May 12, 2014 From the US Patent and Trademark Office Re. U.S. Appl. No. 13/701,558.
Mahler et al. "Rigid, Self-Assembled Hydrogel Composed of a Modified Aromatic Dipeptide", Advanced Materials, XP002446150, 18: 1365-1370, Apr. 25, 2006.
Communication Pursuant to Article 94(3) EPC Dated May 13, 2016 From the European Patent Office Re. Application No. 11730085.5.

* cited by examiner

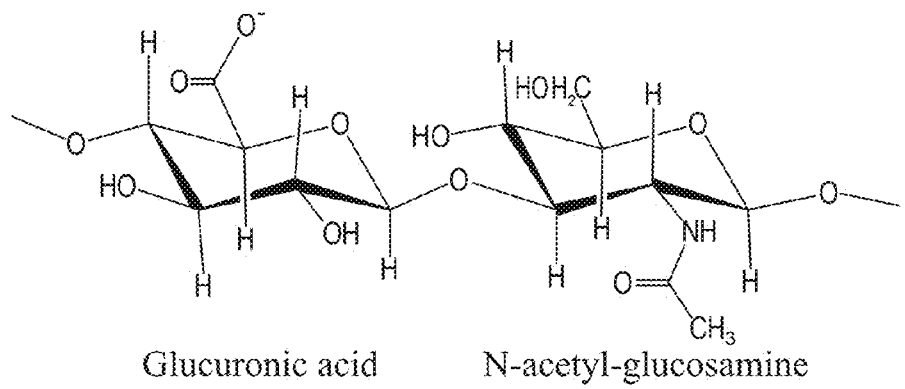
Glucuronic acid    N-acetyl-glucosamine
FIG. 1A
FIG. 1B
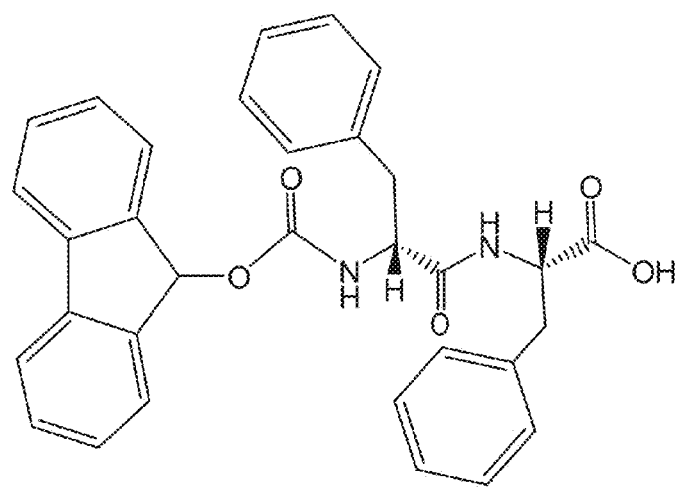
FIG. 2
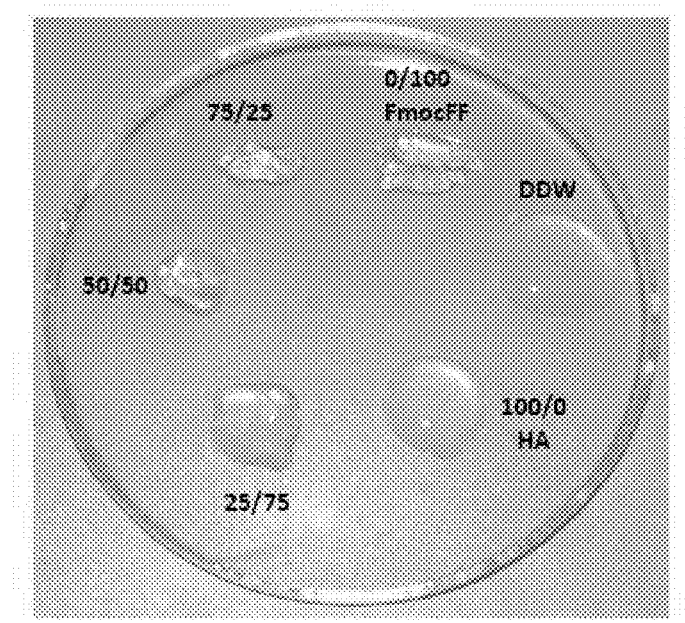

MALLEABLE HYDROGEL HYBRIDS MADE OF SELF-ASSEMBLED PEPTIDES AND BIOCOMPATIBLE POLYMERS AND USES THEREOF

RELATED APPLICATIONS

This application is continuation of U.S. patent application Ser. No. 13/701,558 filed on Dec. 3, 2012, which is a National Phase of PCT Patent Application No. PCT/IL2011/000435 having International filing date of Jun. 2, 2011, which claims the benefit of priority under 35 USC §119(e) of U.S. Provisional Patent Application No. 61/350,978 filed on Jun. 3, 2010. The contents of the above applications are all incorporated by reference as if fully set forth herein in their entirety.

FIELD AND BACKGROUND OF THE INVENTION

The present invention, in some embodiments thereof, relates to novel biomaterials and, more particularly, but not exclusively, to malleable hybrid hydrogels made of peptide(s) and polymer(s).

Biomaterials for tissue engineering are required to possess unique characteristic features for allowing proper biocompatibility, supporting growth and handy biomechanical properties enabling injectability and malleability of the matrix substances.

Development of malleable polymeric nanofiber constructs is of a great scientific and technological interest due to their wide-range applications in biomedicine and biotechnology. Particularly, composite nanofibers derived from natural and synthetic polymers, combining the favorable biological properties of the natural polymer and the mechanical strength of the synthetic polymer, represents a major advantageous advancement in tissue engineering and regenerative medicine.

Hydrogels are determined as polymer networks that are insoluble in water, where they swell to an equilibrium volume but retain their shapes. Hydrogels are of great interest as a class of materials for tissue engineering and regenerative medicine, as they offer 3D scaffolds to support the growth of cultured cells. In terms of material requirements, hydrogels have long received attention because of their innate structural and compositional similarities to the extracellular matrix and their extensive framework for cellular proliferation and survival.

A variety of natural polymers, including agarose, collagen, fibrin, alginate, gelatin, chitosan and hyaluronic acid (HA), may be used as hydrogel-forming materials [Almany and Seliktar 2005, *Biomaterials* 26: 2467-2477]. These polymers are appealing for medical use owing to their similarity to the natural extracellular matrix (ECM), which allows cell adhesion, migration and proliferation, while maintaining very good biocompatible and biodegradable qualities.

Another class of building blocks for hydrogel formation includes synthetic materials, such as poly(ethylene oxide), poly(vinyl alcohol) and poly[furmarate-co-(ethylene glycol)]. These synthetic building blocks offer controllability and reproducibility, but several drawbacks include their production methods that sometimes involve the use of extreme temperatures and pressures and the use of complex techniques, as well as low biocompatibility of the products.

Hydrogels can be prepared either by production of chemical gels or by production of physical gels. Chemical hydrogels are produced by crosslinking starting materials, through chemical or polymerization reactions, and hence involve covalent linking of the hydrogel networks. Physical hydrogels are receiving a great attention since their production does not involve chemical reactions, a fact which is advantageous in the context of encapsulation of cells and other sensitive molecules therein, since laborious removal of toxic or extremely reactive molecules used to initiate chemical crosslinking reactions is circumvented. In physical hydrogels, the networks are held together by molecular entanglements, and/or secondary forces including electrostatic forces, hydrogen-bonding forces or hydrophobic forces [Campoccia et al. 1998 Biomaterials 19: 2101-2127; Prestwich et al. 1998 *J. Controlled Release* 53: 93-103].

Hyaluronic acid (HA) is a high molecular weight unsulfated glycosaminoglycan (GAG) present in all mammals. HA is composed of repeating disaccharide units composed of ($\beta$-1,4)-linked D-glucuronic acid and ($\beta$-1,3)-linked N-acetyl-D-glucosamine (see, FIG. 1A). GAG, a major component of the native extracellular matrix (ECM), is known to support enhanced cell attachment and proliferation and to improve the material's cellular and tissue biocompatibilities. HA in the body occurs as its sodium salt form hyaluronate and is found in high concentrations in the fetus, umbilical cord, and in several soft connective tissues of adults, including skin, synovial fluid, and vitreous humor.

Being a highly hydrated, negatively charged, linear biodegradable and biocompatible natural polymer, characterized by high viscoelastic and space filling properties, HA is highly useful for tissue engineering applications. The advantageous rheological features of HA are exploited, for example, in the application of hyaluronan for ophthalmic surgery [Pape and Balazs 1980, *Ophthalmology* 87(7): 699-705.], in the cosmetic field [Duranti et al 1998 *Dermatol. Slug.* 24: 1317-1325], and in the intra-articular treatment of osteoarthritis [Goa and Benfield 1994 *Drugs* 47(3): 536-566].

However, the use of HA is limited by its poor mechanical strength and by its rapid in vivo enzymatic digestion by hyaluronidase. Overcoming these limitations can be made by introducing synthetic cross-linkers, for providing strengthen HA composite with reduced biodegradation rate [Leach et al. 2003 *Biotechnol. Bioeng.* 82(5), 578-589; Lu et al. 2008 *J. Biomater. Sci. Polym.* 19:1-18; and Pitarresi et al. 2008 *J. Biomed. Mater. Res, Part A* 84A(2): 413-424], and/or by employing specific or non-specific inhibitors of hyaluronidase.

Self-assembled nanotubes and hydrogels made of short (aromatic) peptides have been disclosed in Mahler et al. *Adv. Mater.* 18: 1365-1370, and in WO 2007/0403048, WO 2004/052773 and WO 2004/060791. An exemplary building block for forming such nanotubes and hydrogels is Fmoc-FF.

Fmoc-FF is a protected dipeptide, which was shown to self-assemble into discrete, well-ordered nanotubes and to form hydrogels in the macrostructure. The diphenylalanine peptide (FF) is the natural core recognition motif of the amyloid-$\beta$polypeptide. The Fmoc group (9-fluorenylmethoxycarbonyl) is widely used as a synthetic protecting group in peptide synthesis and it was reported by Burch et al. that a number of Fmoc-amino acids show anti-inflammatory properties [Burch et al. 1991 *Proc. Natl. Acad. Sci. U.S.A.* 88: 355-359].

The efficient self-assembly, under mild conditions, of Fmoc-FF into a hydrogel which exhibits remarkable physical properties has been reported (see, Mahler et al., supra). In spite of the short building-block size, the obtained hydrogel was characterized by physical properties that exceed those of hydrogels formed from longer polypeptides.

Hybrid composite hydrogels are reviewed, for example, in Jia and Kiick in Macromol Biosci. 2009 Feb. 11; 9(2): 140-156, and references cited therein. Several hybrid hydrogels made of hyaluronic acid and polymers such as PEG, chitosan, cellulose and alginate have been reported. Hybrid hydrogels made of hyaluronic acid and other polysaccharides and proteins such as collagen, gelatin and fibrin have also been reported. Hydrogel matrices made of hyaluronic acid derivatized by a cell adhesive peptide fragment are disclosed, for example, in U.S. Pat. Nos. 5,834,029 and 6,156,572. Hydrogels made of hyaluronic acid modified with Nodo-66 antagonist have been reported in Hou et al., J. Neurosci. Met. 137:519-529, 2005.

Additional background art includes Yang et al., Biomedical Materials, 2001, 6, 025009; Kim et al., Acta Biomater. 2008, 4(6):1611-1619; and Park et al., Key engineering materials, Vols. 342-343 (2007), pp. 153-156.

SUMMARY OF THE INVENTION

According to an aspect of some embodiments of the present invention there is provided a hydrogel comprising a fibrous network of a plurality of peptides and hyaluronic acid, wherein each peptide in the plurality of peptides is a dipeptide which comprises at least one aromatic amino acid residue.

According to some embodiments of the invention, at least one of the dipeptides consists of aromatic amino acid residues.

According to some embodiments of the invention, each of the dipeptides consists of aromatic amino acid residues.

According to some embodiments of the invention, at least one dipeptide in the plurality of dipeptides is a homodipeptide.

According to some embodiments of the invention, each of the dipeptides is a homopeptide.

According to some embodiments of the invention, each of the dipeptides is phenylalanine-phenylalanine dipeptide (Phe-Phe).

According to some embodiments of the invention, at least one dipeptide in the plurality of peptides is an end-capping modified peptide.

According to some embodiments of the invention, each dipeptide in the plurality of dipeptides is an end-capping modified peptide.

According to some embodiments of the invention, each of the end-capping modified dipeptides comprises an aromatic end-capping moiety.

According to some embodiments of the invention, the aromatic end capping moiety is 9-fluorenylmethyloxycarbonyl (Fmoc).

According to an aspect of some embodiments of the invention there is provided a hydrogel comprising a fibrous network of a plurality of peptides and at least one biocompatible polymer, wherein the peptides are capable of self-assembling in an aqueous solution so as to form a hydrogel and wherein the biocompatible polymer features at least one characteristic selected from the group consisting of: (i) a storage modulus G' lower than 500 Pa at 10 Hz frequency and at 25° C.; (ii) a swelling ratio (Q) higher than 500; (iii) a viscosity at 0.1 Sec$^{-1}$ shear rate and at 25° C., lower than 300 Pa·s; and (iv) a viscosity recovery after shear of at least 95%.

According to some embodiments of the invention, the biocompatible polymer is a polysaccharide.

According to some embodiments of the invention, the biocompatible polymer is hyaluronic acid.

According to some embodiments of the invention, the biocompatible polymer is a chitosan.

According to some embodiments of the invention, the biocompatible polymer has an average molecular weight that ranges from 10 kDa to 10,000 kDa.

According to some embodiments of the invention, each peptide in the plurality of peptides comprises an amino acid sequence not exceeding 6 amino acids in length, whereas the amino acid sequence comprises at least one aromatic amino acid residue.

According to some embodiments of the invention, at least one peptide in the plurality of peptides consists essentially of aromatic amino acid residues.

According to some embodiments of the invention, each peptide in the plurality of peptides consists essentially of aromatic amino acid residues.

According to some embodiments of the invention, at least one peptide in the plurality of peptides is a dipeptide.

According to some embodiments of the invention, each peptide in the plurality of peptides is a dipeptide.

According to some embodiments of the invention, at least one of the dipeptides is a homodipeptide.

According to some embodiments of the invention, each of the dipeptides is a homopeptide.

According to some embodiments of the invention, the homodipeptide is selected from the group consisting of phenylalanine-phenylalanine dipeptide, naphthylalanine-naphthylalanine dipeptide, phenanthrenylalanine-phenanthrenylalanine dipeptide, anthracenylalanine-anthracenylalanine dipeptide, [1,10]phenanthrolinylalanine-[1,10]phenanthrolinylalanine dipeptide, [2,2']bipyridinylalanine-[2,2']bipyridinylalanine dipeptide, (pentahalo-phenylalanine)-(pentahalo-phenylalanine) dipeptide, (amino-phenylalanine)-(amino-phenylalanine) dipeptide, (dialkylamino-phenylalanine)-(dialkylamino-phenylalanine) dipeptide, (halophenylalanine)-(halophenylalanine) dipeptide, (alkoxy-phenylalanine)-(alkoxy-phenylalanine) dipeptide, (trihalomethyl-phenylalanine)-(trihalomethyl-phenylalanine) dipeptide, (4-phenyl-phenylalanine)-(4-phenyl-phenylalanine) dipeptide and (nitro-phenylalanine)-(nitro-phenylalanine) dipeptide.

According to some embodiments of the invention, at least one peptide in the plurality of peptides is an end-capping modified peptide.

According to some embodiments of the invention, each peptide in the plurality of peptides is an end-capping modified peptide.

According to some embodiments of the invention, the end capping modified peptide comprises at least one end capping moiety, the end capping moiety being selected from the group consisting of an aromatic end capping moiety and a non-aromatic end-capping moiety.

According to some embodiments of the invention, the aromatic end capping moiety is 9-fluorenylmethyloxycarbonyl (Fmoc).

According to some embodiments of the invention, a total concentration of the plurality of peptides and the polymer ranges from 0.1 weight percent to 5 weight percents of the total weight of the gel.

According to some embodiments of the invention, the total concentration ranges from 0.5 weight percent to 2.5 weight percent of the total weight of the gel.

According to some embodiments of the invention, a weight ratio of the dipeptides and the polymer ranges from 10:1 to 1:10.

According to some embodiments of the invention, the ratio ranges from 3:1 to 1:3.

According to some embodiments of the invention, the fibrous network comprises a plurality of fibrils, whereas an average diameter of the fibrils ranges from about 10 nm to about 100 nm.

According to some embodiments of the invention, the hydrogel is characterized by a storage modulus G' to loss modulus G" ratio that is higher by at least 2-folds than the ratio of the biocompatible polymer.

According to some embodiments of the invention, the hydrogel is characterized by a storage modulus G' that is lower by at least 10% of a storage modulus G' of a hydrogel formed of the plurality of peptides.

According to some embodiments of the invention, the hydrogel is characterized by a storage modulus G' that is higher by at least 5-folds of a storage modulus G' of the biocompatible polymer.

According to some embodiments of the invention, the hydrogel is characterized by a swelling ratio (Q) higher by at least 5% of a swelling ratio of a hydrogel formed of the plurality of peptides.

According to some embodiments of the invention, the hydrogel is characterized by a viscosity higher by at least 10% of a viscosity of the biocompatible polymer.

According to some embodiments of the invention, the hydrogel is characterized by a viscosity change through time higher by at least 2-folds than a viscosity change through time of the biocompatible polymer.

According to some embodiments of the invention, the hydrogel is characterized by biocompatibility to cell viability higher by at least 2-folds than a biocompatibility to cell viability of a hydrogel formed of the plurality of peptides.

According to some embodiments of the invention, the hydrogel is characterized by a storage modulus G' to loss modulus G" ratio that is greater than 4.

According to some embodiments of the invention, the hydrogel is characterized by a storage modulus G' higher than 1,000 Pa at 10 Hz frequency and at 25° C.

According to some embodiments of the invention, the hydrogel is characterized by a storage modulus G' lower than 100,000 Pa at 10 Hz frequency and at 25° C.

According to some embodiments of the invention, the hydrogel is characterized by a viscosity that ranges from 200 to 2000 Pa·s at 0.1 $Sec^{-1}$ shear rate, at 25° C.

According to some embodiments of the invention, the hydrogel is characterized by a viscosity recovery after shear of at least 50%, at 0.1 $sec^{-1}$.

According to some embodiments of the invention, the hydrogel is characterized by a swelling ratio (Q) that ranges from 100 to 500.

According to an aspect of some embodiments of the invention there is provided a composition-of-matter comprising the hydrogel as described herein and at least one agent being incorporated therein or thereon.

According to some embodiments of the invention, the agent is selected from the group consisting of a therapeutically active agent, a diagnostic agent, a biological substance and a labeling moiety.

According to some embodiments of the invention, the agent is selected from the group consisting of a drug, a cell, a nucleic acid, a fluorescence compound or moiety, a phosphorescence compound or moiety, a protein, an enzyme, a hormone, a growth factor, a bacterium and a radioactive compound or moiety.

According to an aspect of some embodiments of the invention there is provided a process of preparing the hydrogel as described herein, the process comprising contacting the plurality of peptides and the biocompatible polymer in an aqueous solution.

According to some embodiments of the invention, the contacting comprises dissolving the polymer in the aqueous solution and contacting the peptides with the aqueous solution.

According to some embodiments of the invention, a total concentration of the plurality of peptides and the polymer in the aqueous solution ranges from about 0.1 mg/ml to about 50 mg/ml.

According to some embodiments of the invention, the process further comprises, prior to the contacting, dissolving the plurality of peptides in a water-miscible organic solvent.

According to some embodiments of the invention, the contacting is effected ex-vivo.

According to some embodiments of the invention, the contacting is effected in-vivo.

According to some embodiments of the invention, the contacting is effected at a desired site of application of the hydrogel.

According to an aspect of some embodiments of the invention there is provided a pharmaceutical, cosmetic or cosmeceutical composition comprising the hydrogel of as described herein.

According to some embodiments of the invention, the composition further comprises a pharmaceutically acceptable carrier.

According to an aspect of some embodiments of the invention there is provided a pharmaceutical, cosmetic or cosmeceutical composition comprising the composition-of-matter as described herein.

According to an aspect of some embodiments of the invention there is provided an article-of-manufacture comprising the hydrogel, composition-of-matter or composition as described herein.

According to an aspect of some embodiments of the invention there is provided a kit for forming the hydrogel as described herein, the kit comprising the plurality of peptides and the biocompatible polymer.

According to some embodiments of the invention, the kit further comprises instructions for forming the hydrogel by contacting the peptides and the biocompatible polymer with an aqueous solution.

According to some embodiments of the invention, the kit further comprises an aqueous solution, wherein the peptides and the aqueous solution are individually packaged within the kit.

According to some embodiments of the invention, the polymer is dissolved in the aqueous solution.

According to an aspect of some embodiments of the invention there is provided a kit of for forming the composition-of-matter as described herein, the kit comprising the plurality of peptides, the biocompatible polymer and the active agent.

According to some embodiments of the invention, the kit further comprises instructions for forming the hydrogel by contacting the plurality of peptides, the biocompatible polymer and the active agent with an aqueous solution.

According to some embodiments of the invention, the kit further comprises an aqueous solution, wherein the plurality of peptides and the aqueous solution are individually packaged within the kit.

According to some embodiments of the invention, the polymer is dissolved in the aqueous solution.

According to some embodiments of the invention, each of the hydrogel, the composition-of-matter or the composition described herein is identified for use in repairing a damaged tissue.

According to an aspect of some embodiments of the invention there is provided a use of the hydrogel, the composition-of-matter or the composition as described herein in the manufacturing of a medicament for repairing a damaged tissue.

According to an aspect of some embodiments of the invention there is provided a method of repairing a damaged tissue, the method comprising contacting the damaged tissue with the hydrogel, the composition-of-matter or the composition as described herein.

According to an aspect of some embodiments of the invention there is provided a method of repairing a damaged tissue comprising contacting the damaged tissue with a mixture comprising a plurality of peptides and a biocompatible polymer, wherein the peptides are capable of self-assembling in an aqueous solution so as to form a hydrogel and wherein the biocompatible polymer features at least one characteristic as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B present the chemical structures of hyaluronic acid (HA, FIG. 1A) and Fmoc-diphenylalanine (Fmoc-FF, FIG. 1B), exemplary building block of the hybrid hydrogels according to some embodiments of the present invention;

FIG. 2 is a photograph showing the hydrogel macrostructure of hydrogels made of pure components (DDW, Fmoc-FF and HA) and of hybrid hydrogels made from different weight ratios of Fmoc-FF/HA;

FIGS. 3A-C present images showing the hydrogel microstructure of hydrogels made of HA (1), 25/75 Fmoc-FF/HA (2), 50/50 Fmoc-FF/HA (3), 75/25 Fmoc-FF/HA (4) and Fmoc-FF (5), as observed by TEM (FIG. 3A), SEM (FIG. 3B) and E-SEM (FIG. 3C);

Figure 6:
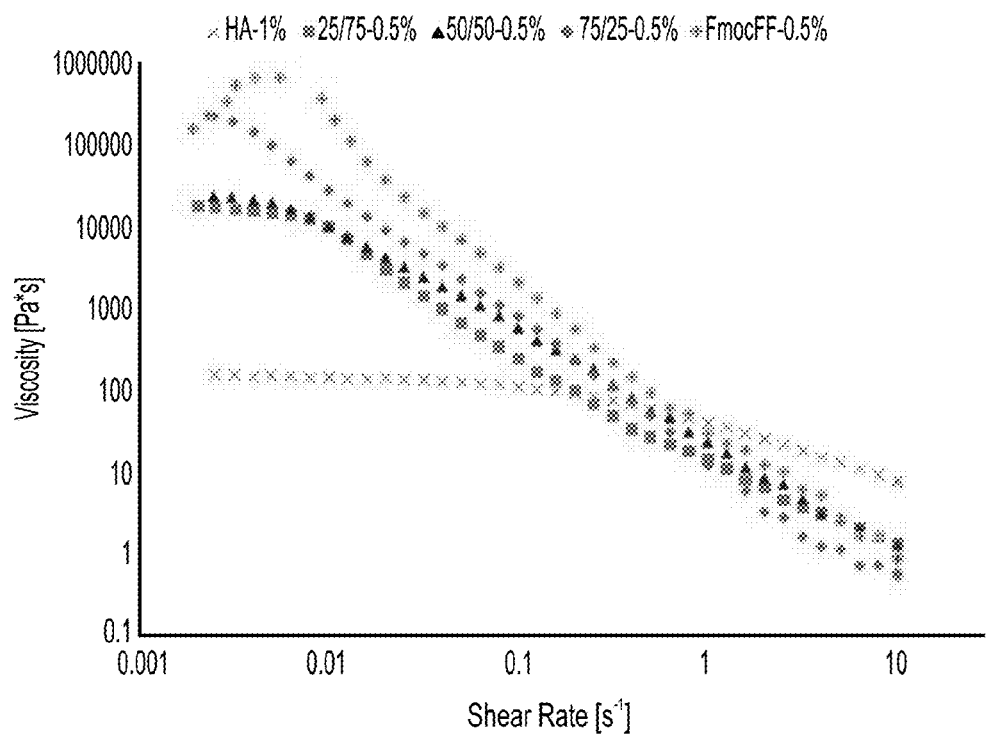
Figure 7:
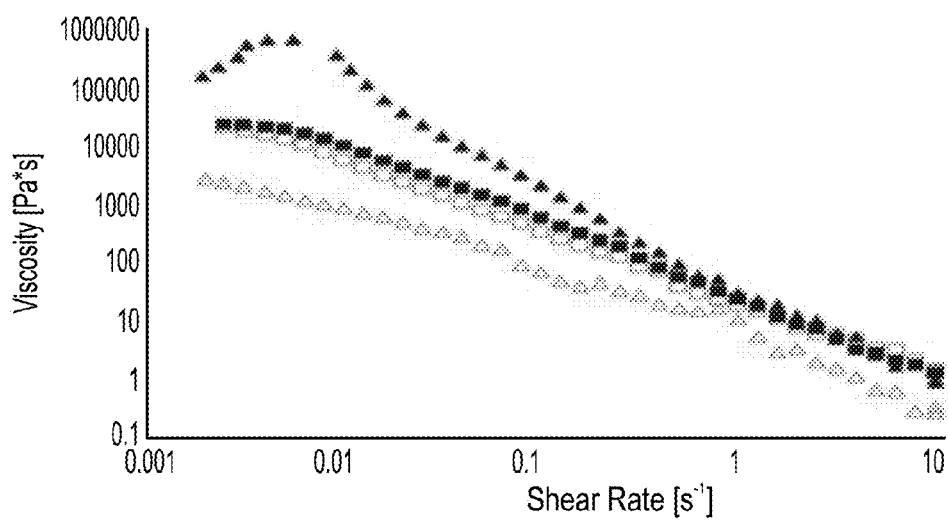
Figure 8:
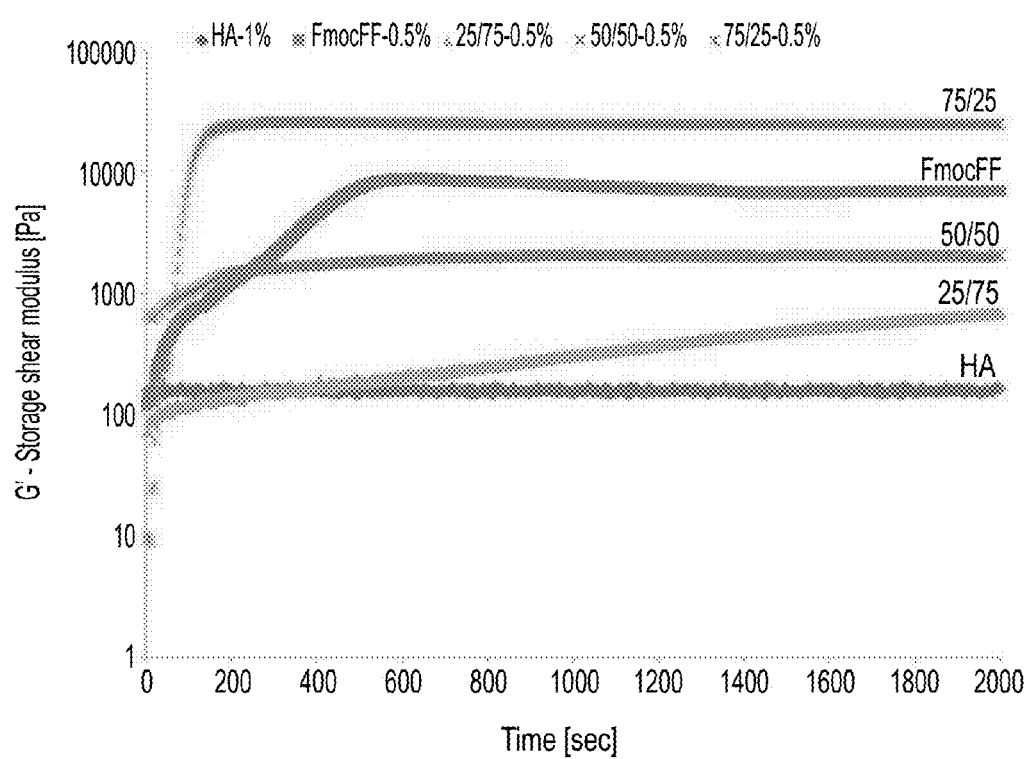
Figure 9:
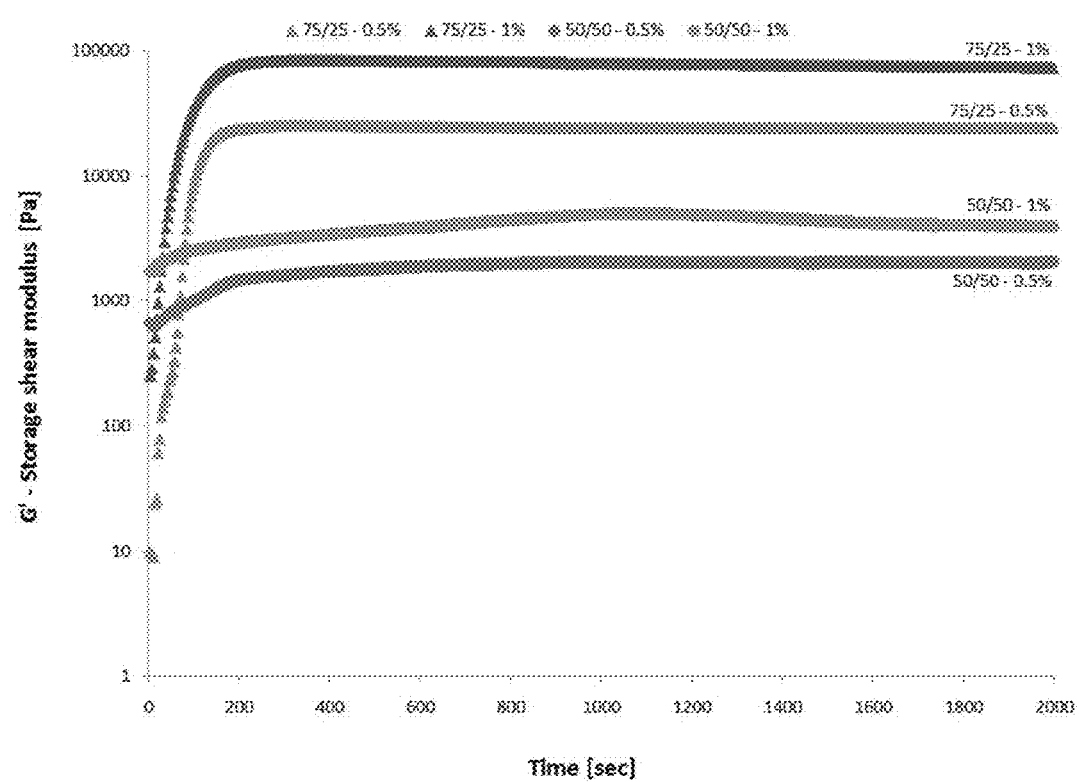
Figure 10:
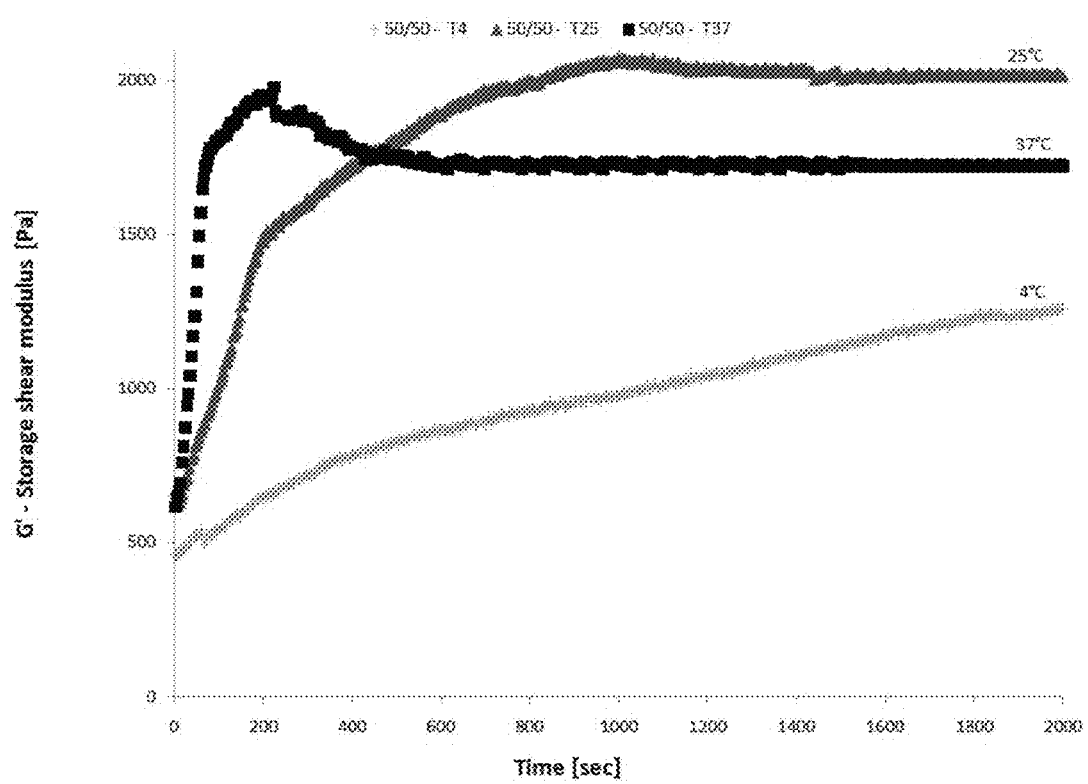
Figure 11:
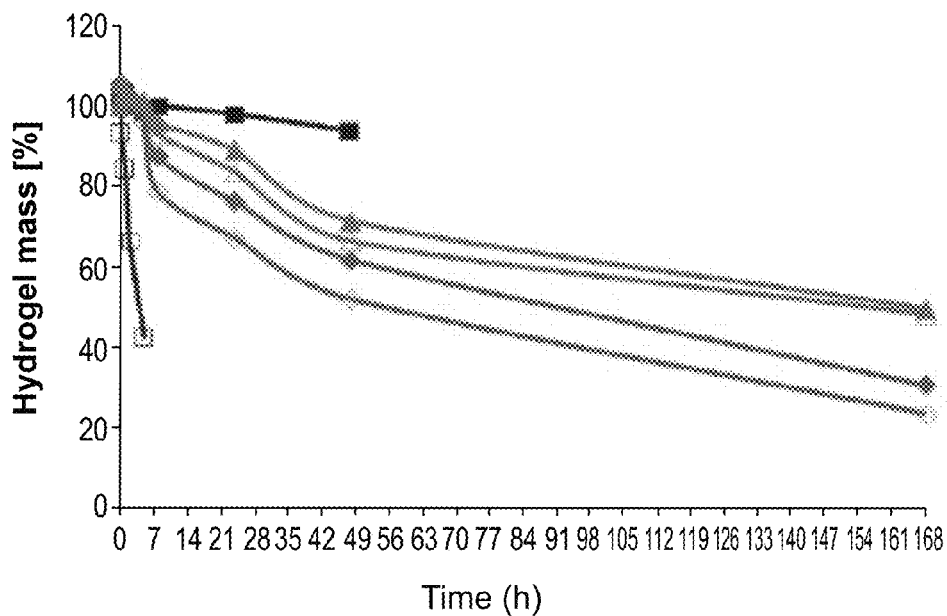
Figure 12:
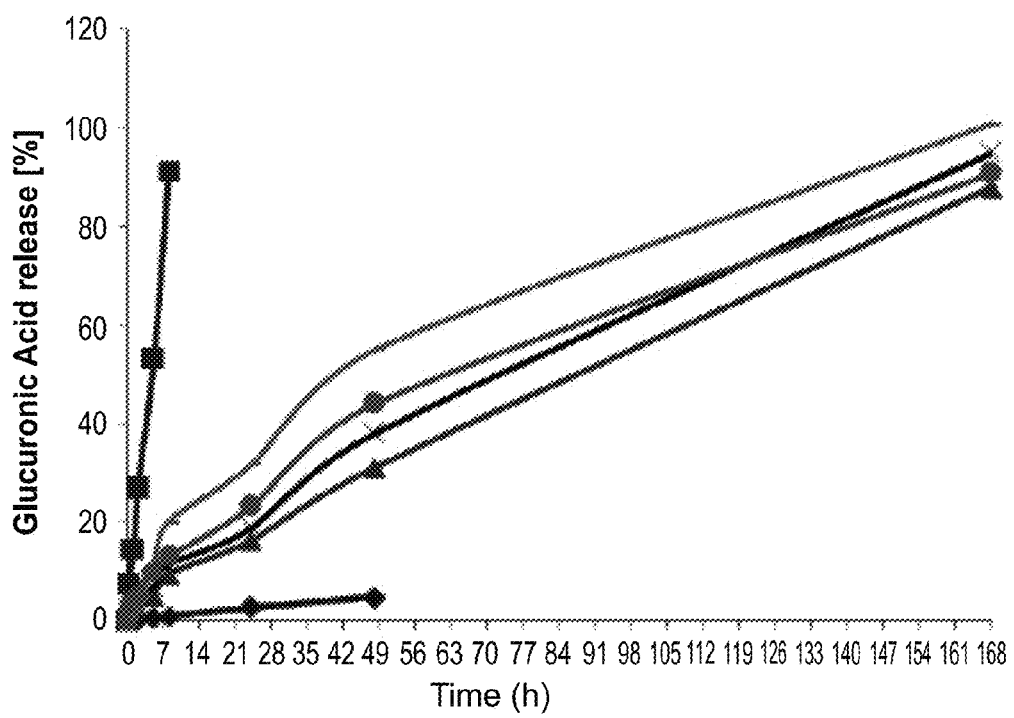
Figure 13:
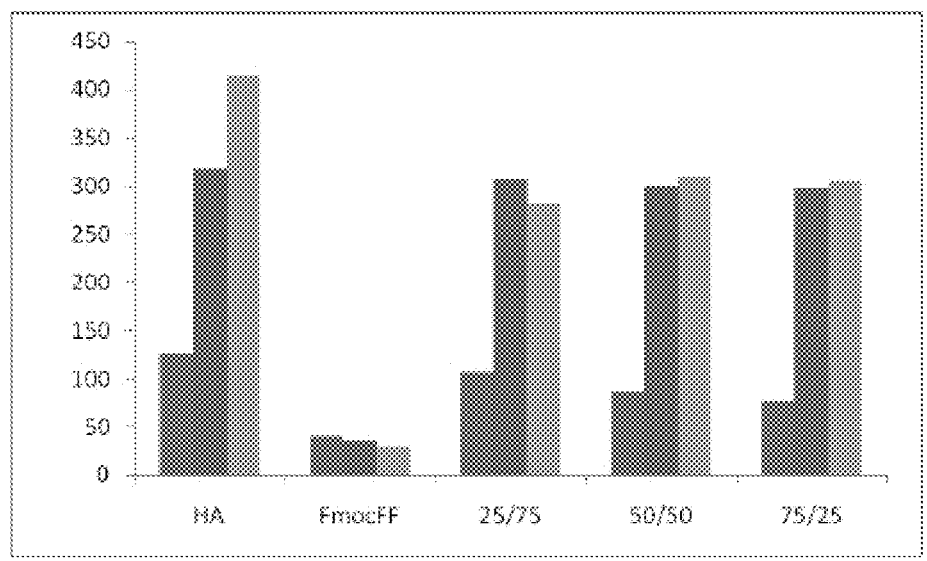
Figure 14:
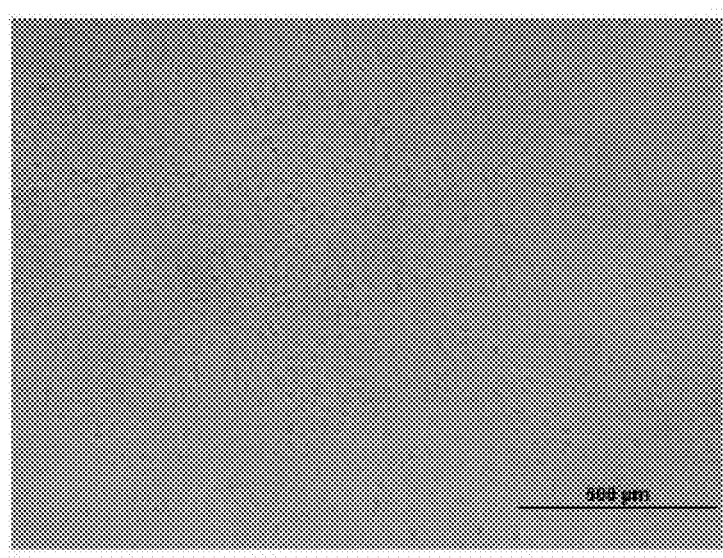
Figure 15A:
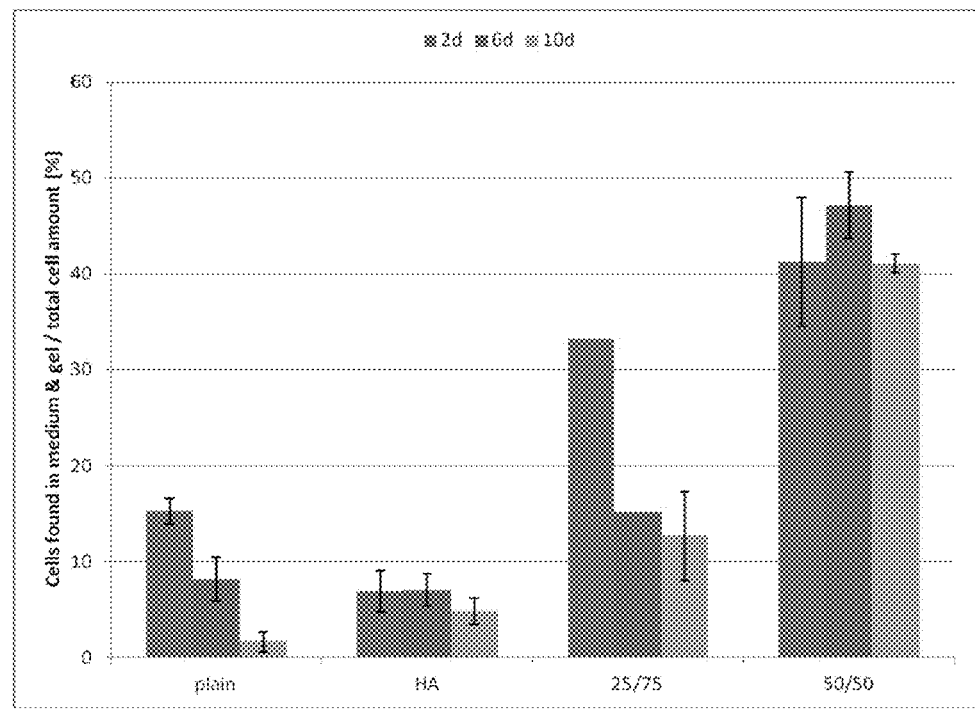
Figure 15B:
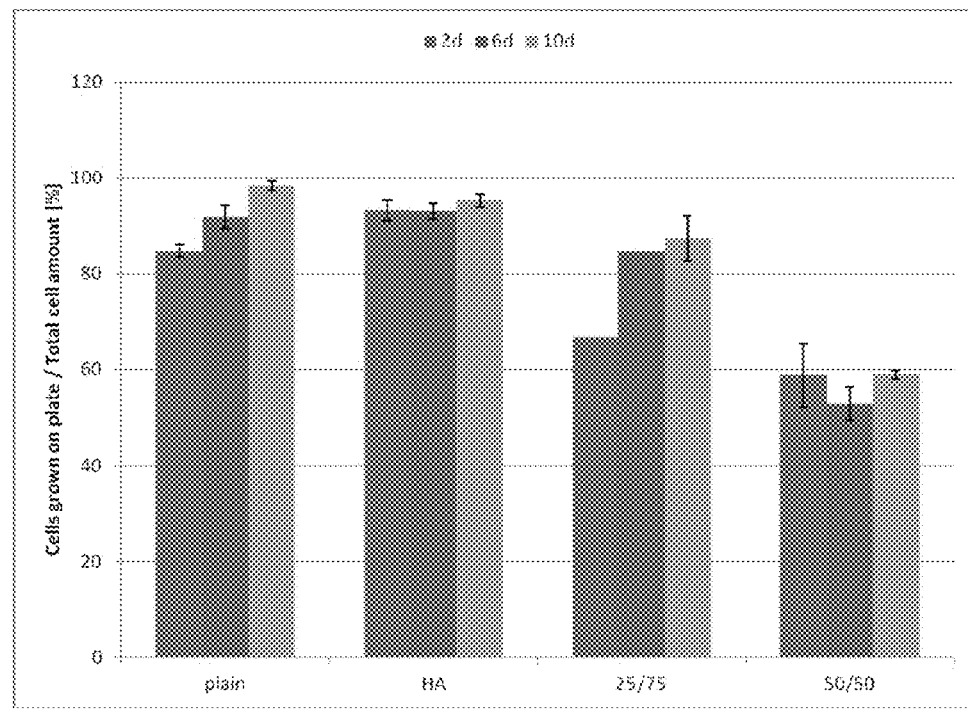
Figure 16A:
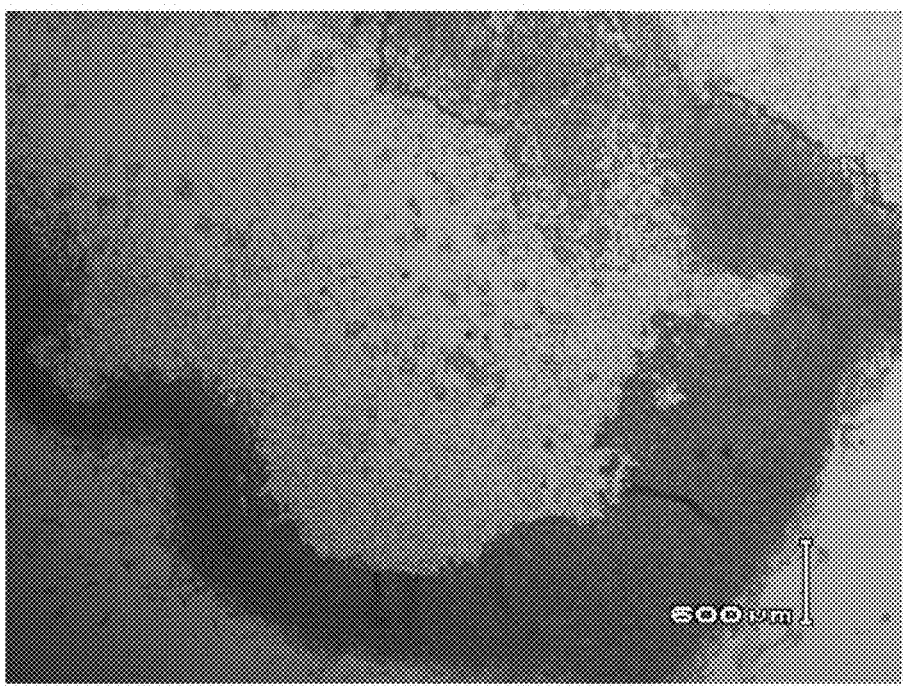
Figure 16B:
Figure 16C:

FIG. 6 presents comparative plots showing the viscosity at room temperature of hydrogels made of HA (1%; black Xs), 25/75 Fmoc-FF/HA (0.5%; red squares), 75/25 Fmoc-FF/HA (0.5%; blue diamonds), 50/50 Fmoc-FF/HA (black triangles) and Fmoc-FF (0.5%, black +);

FIG. 7 presents comparative plots showing the values obtained in an elasticity test measuring the viscosity recovery after shear of a 50/50 Fmoc-FF/HA hybrid hydrogel and of a Fmoc-FF hydrogel, with black triangles representing data for Fmoc-FF hydrogel at t=0, blank triangles of Fmoc-FF hydrogel at t=10, black circles representing data for a 50/50 Fmoc-FF/HA hybrid hydrogel at t=0 and blank circles of 50/50 Fmoc-FF/HA at t=10;

FIG. 8 presents comparative plots showing the rheological properties (measured at 25° C.) of hydrogels made of the pure components Fmoc-FF (red) and HA (blue) and of hybrid hydrogels made from 25/75 Fmoc-FF/HA (green), 75/25 Fmoc-FF/HA (cyan Xs) and 50/50 Fmoc-FF/HA (purple);

FIG. 9 presents comparative plots showing the rheological properties (measured at 25° C.) of hydrogels made of 75/25 Fmoc-FF/HA at a concentrations of 0.5% (green triangles) and 1% (purple triangles) and of 50/50 Fmoc-FF/HA at a concentration of 0.5% (blue circles) and 1% (orange circles);

FIG. 10 presents comparative plots showing the effect of the temperature on the rheological properties of an exemplary hybrid hydrogel made from 50/50 Fmoc-FF/HA at 4° C. (blue), 25° C. (red) and 37° C. (black);

FIG. 11 presents comparative plots showing the hydrogel mass loss with time for solutions made of HA in the absence (filled black squares) and presence (blank black squares) of Hyaluronidase, and for hybrid hydrogels made of 25/75 Fmoc-FF/HA in the absence (filled red diamonds) and presence (blank red diamonds) of Hyaluronidase, and of 50/50 Fmoc-FF/HA in the absence (filled green triangles) and presence (blank green triangles) of Hyaluronidase;

FIG. 12 presents comparative plots showing release of glucuronic acid with time from solutions made of HA in the absence (blue diamonds) and presence (red squares) of Hyaluronidase, from hydrogels made of 25/75 Fmoc-FF/HA in the absence (orange circles) and presence (purple lines) of Hyaluronidase, and from hydrogels made of 50/50 Fmoc-FF/HA in the absence (green triangles) and presence (gray Xs) of Hyaluronidase;

FIG. 13 is a bar graph showing CHO (Chinese Hamster Ovaries) cells viability 1 day (blue), 3 days (red) and 7 days (green) post seeding the cell on a 50/50 Fmoc-FF/HA exemplary hydrogel according to some embodiments of the invention;

FIG. 14 presents a light micrograph of chondrocytes grown on a hybrid hydrogel made of 50/50 Fmoc-FF/HA, one day post seeding;

FIGS. 15A-B are bar graphs presenting the percents of cells found in medium and gel out of the total cell amount at different time points (FIG. 15A), and the percents of cells found grown on the plate out of the total cell amount at different time points (FIG. 15B), upon seeding cells on top of an HA solution, a 25/75 Fmoc-FF/HA hydrogel and a 50/50 Fmoc-FF/HA, as measured 2 days (blue), 6 days (red) and 10 days (green) post seeding; and FIGS. 16A-C are light micrographs of H&E staining of limb-buds embedded in 50/50 Fmoc-FF/HA hybrid hydrogel after 6 days on a CAM of an 8-day fertilized chicken egg (X 25), presenting an initial stage of limb-bud (FIG. 16A), chondrocytes condensation (FIG. 16B), and organogenesis into limb formation (FIG. 16C).

DESCRIPTION OF SPECIFIC EMBODIMENTS OF THE INVENTION

The present invention, in some embodiments thereof, relates to novel biomaterials and, more particularly, but not exclusively, to malleable hybrid hydrogels made of peptides and polymers.

Before explaining at least one embodiment of the invention in detail, it is to be understood that the invention is not necessarily limited in its application to the details set forth in the following description or exemplified by the Examples.

In view of the recognized need for mimics of extracellular matrix (ECM) in biomaterial applications such as tissue engineering, extensive efforts have been made for designing structures that mimic the hybrid nature of the natural ECM. To this effect, multicomponent hybrid hydrogels have been developed by integrating modular and heterogeneous building blocks into multifunctional hydrogel composites.

As further discussed hereinabove, hydrogels are the most appealing candidates for tissue engineering scaffolds due to their structural similarity to the natural ECM, inherent biocompatibility, tunable viscoelasticity, high water content and high permeability for oxygen and essential nutrients.

Hyaluronic acid represents a desirable component for hydrogel formation due to its exceptional biocompatibility, swelling capability and viscoelasticity. The fast biodegradation of HA, however, limits its use in tissue engineering applications. Similar properties are exhibited also by other polysaccharides, as is further detailed hereinbelow.

Hydrogels made of self-assembled peptides have been reported, for example, in Mahler et al. Adv. Mater. 18: 1365-1370, and in WO 2007/0403048. Exemplary such hydrogels, formed from Fmoc-FF, were shown to exhibit exceptional mechanical strength. Such a high rigidity is often not desired in tissue engineering or regeneration applications, which require malleability, and further, render such hydrogels less suitable matrices for maintaining or promoting cellular activity, as further defined hereinbelow.

In a search for improved hydrogel materials for use in biomaterial applications such as tissue engineering and regeneration, the present inventors have designed and successfully practiced a novel approach for creating hybrid hydrogel composites which combine the properties of biocompatible polymers that are suitable matrices for cell growth with the mechanical properties of self-assembled peptides, while circumventing the use of chemical cross-linking.

While conceiving the present invention, it was envisioned that combining the beneficial properties of biocompatible polymers that have high swelling capability and viscoelasticity with the mechanical strength imparted by self-assembled peptides would result in composite substances that integrate these beneficial properties.

While reducing the present invention to practice, the present inventors have indeed demonstrated that mixing such components under conditions that facilitate hydrogel formation (e.g., at suitable concentrations in an aqueous solution), without using any chemical crosslinking agents, results in hydrogels that are characterized both by a remarkable rigidity and biocompatibility. The present inventors have surprisingly uncovered that the obtained hybrid hydrogels exhibit averaged properties of the two components, such that the rheological, viscoelastic, swelling and biodegradability properties of the hybrid hydrogel can be finely tuned by means of varying the concentration ratio of the two components.

The present inventors have demonstrated that well-blended composite hydrogels that integrate the favorable biological properties of biocompatible polymers and the mechanical properties of self-assembled peptides significantly improve the material properties, while providing a stable, nurturing environment for a broad array of biomedical applications.

This novel approach was shown to improve the mechanical properties of biocompatible polymers such as hyaluronic acid, which are otherwise characterized by limited mechanical strength and sometimes by fast degradation, and on the same time, to improve the biocompatibility of self-assembled peptidic hydrogels, by reducing the rigidity and enhancing the swelling capability thereof, and thus by rendering malleable hydrogels and more suitable matrices for cell growth.

As demonstrated in the Examples section that follows, hybrid hydrogels comprised of hyaluronic acid (HA; see, FIG. 1A) as an exemplary biocompatible polymer and Fmoc-FF (fluorenylmethoxycarbonyl-diphenylalanine; see, FIG. 1B) as an exemplary a self-assembled peptide were prepared and characterized.

HA is a biodegradable, non-immunogenic, and biocompatible natural polymer, which represents remarkable viscoelastic properties, and is an attractive biomaterial for cells in tissue engineering. Fmoc-FF is a short peptide with a protected group (Fmoc), which was shown to self-assemble into remarkably rigid hydrogel microstructure.

A set of hybrid hydrogels with varying concentration ratios between the two components was successfully prepared and was shown to exhibit a controllable malleability. Thus, for example, it was shown that in higher peptide concentrations less swelling is attained, and the hydrogel represents more dense and rigid features, contributing to slower biodegradation. The hydrogel hybrids exhibit desirable mechanical properties (rheological-shear stress, viscosity, recovery after shear) with high biocompatibility for various cells. It has been shown that HA improves the hydrogel hybrid elasticity, and contributes to cell adhesion and biocompatibility, whereas Fmoc-FF improves the hydrogel hybrid mechanical features (shear stress), and slowing down the HA degradation (probably due to less penetration of the degrading enzyme).

Thus, it has been shown that the blended hybrid reflects moderate, averagable biomechanical features, ranging in between the pure elements. Hybrid hydrogels were also successfully prepared from Fmoc-FF and chitosan.

According to an aspect of some embodiments of the present invention there is provided a hydrogel comprising a fibrous network of a plurality of peptides and a biocompatible polymer.

In some embodiments, the plurality of peptides comprises peptides which are capable of self-assembling in an aqueous solution so as to form a hydrogel.

As noted hereinabove, self-assembling peptides typically form relatively rigid structures which render hydrogels formed therefrom less suitable for biomaterial applications that typically require malleable matrices suitable for cell growth, for transport of biological substance.

As further discussed hereinabove, it has been demonstrated herein that hydrogels made of self-assembling peptides can be rendered suitable for biomaterial applications upon forming a hybrid hydrogel which comprises such peptides and a polymer that imparts biocompatibility to the hydrogel by featuring characteristics such as elasticity, high swelling capability and/or lower mechanical strength compared to the self-assembling peptides.

To this end, biocompatible polymers suitable for use within the hydrogels described herein are selected as featuring one or more of the following characteristics:

(i) a storage modulus G' lower than 500 Pa at 10 Hz frequency and at 25° C., which is indicative of a polymer with relatively low mechanical strength;

(ii) a swelling ratio (Q) higher than 500, which is indicative of high hydration capability of the polymer;

(iii) a viscosity at 0.1 Sec$^{-1}$ shear rate and at 25° C., lower than 300 Pa·s; and (iv) a viscosity recovery after shear of at least 95%, which is indicative of elasticity.

As used herein, and is well-known in the art, the term "hydrogel" refers to a material that comprises solid, typically fibrous networks formed, at least in part, of water-soluble natural or synthetic polymer chains, and typically containing more than 90% water, or more than 95% water.

As used herein the phrase "fibrous network" refers to a set of connections formed between the plurality of fibrous components. Herein, the fibrous components are composed, at least in part, of peptide fibrils, each formed upon self-assembly of short peptide building blocks, as is further detailed hereinbelow.

Since the hydrogels described herein are formed of two or more types of components, the hydrogels are also referred to herein interchangeably as "hydrogel hybrid" or "hybrid hydrogel" or "composite" or "hydrogel composite" or "hybrid hydrogel composite" or "hydrogel hybrid composite".

As currently accepted in the art, the term "biocompatible" is generally defined as "the ability of a material to perform with an appropriate host response in a specific application" [see, The Williams dictionary of Biomaterials].

In the context of biomaterial applications such as tissue engineering and regeneration, biocompatibility refers to the ability to perform as a supportive matrix to an appropriate cellular activity, without eliciting any undesirable effects in those cells, or inducing any undesirable local or systemic responses in the host.

In the context of embodiments of the present invention, a "biocompatible material" describes a material (e.g., a natural or synthetic polymer) or matrix (e.g., hydrogel or scaffold) that does not interfere, and preferably provides a suitable environment for, cellular activity.

A "cellular activity" includes, for example, cell viability, cell growth (proliferation), cell differentiation, cell migration, cell adhesion, molecular and mechanical signaling systems, and fluid transport through cells or a tissue so as to allow nutritive environment.

The biocompatibility of a substance can be determined by methods well known in the art, following the definitions hereinabove and international guidelines, using widely recognized safety assays. Optionally, biocompatible substances can be selected from existing lists of such substances.

In the context of the present embodiments, the biocompatible polymer features physical properties as described herein.

Thus, in some embodiments, the biocompatible polymer is characterized by a relatively high swelling ratio.

As used herein and in the art, the phrase "swelling ratio", denoted "Q", describes the ratio between the weight of a swollen substance (Ws) and the weight of dry substance (Wd) and is calculated according to the expression: Q=Ws/Wd.

An exemplary procedure for measuring the weights of swollen and dry substances in presented in the Examples section that follows.

Substances that have high swelling capability typically have a swelling ratio that is higher than 100, higher than 200, higher than 300, higher than 400, preferably higher than 500, higher than 600, higher than 700, higher than 800, higher than 900 and even 1,000.

In the context of embodiments of the invention, a high swelling ratio of the polymer is desired for imparting swelling capability to the formed hybrid hydrogel.

Further in the context of embodiments of the present invention, hydrogels with enhanced swelling capability are beneficial in biomaterial applications.

Biocompatible polymers with high swelling ratio (e.g., 500 or higher) are typically highly-hydrated polymers. Exemplary such polymers include polysaccharides, particularly high molecular weight linear polysaccharides such as the GAGs, chitosan, agarose, alginate and the like.

In some embodiments, the biocompatible polymer is characterized as a viscoelastic substance.

Viscoelasticity is the property of materials that exhibit both viscous and elastic characteristics when undergoing deformation. Viscous materials resist shear flow and strain linearly with time when a stress is applied. Elastic materials strain instantaneously when stretched and return to their original state once the stress is removed. Viscoelastic materials have elements of both of these properties and, as such, exhibit time dependent strain.

Viscoelastic substances have an elastic component and a viscous component. The rheology of viscoelastic substances is therefore typically defined by the Complex Dynamic modulus, G, which represents the relation between the oscillating stress and strain, as follows:

$$G=G'+iG''$$

where $i^2=-1$; G' is the storage modulus (representing elastic modulus) and G" is the loss modulus (representing frictional modulus).

Since it is desirable that the biocompatible polymer would impart elasticity to the formed hydrogel hybrid, is some embodiments, the biocompatible polymer is characterized by relatively low storage modulus G', being lower than 500, lower than 400, lower than 300, or lower than 200.

In some embodiments, a biocompatible polymer is characterized by a relatively low ratio of shear storage modulus to loss modulus. In some embodiments, this ratio is lower than 1.

In some embodiments, the elasticity of the biocompatible polymer is determined by a change of viscosity through time and/or by viscosity recovery after shear, as exemplified in the Examples section that follows.

Viscosity is a measure of the resistance of a fluid which is being deformed by, for example, shear stress. Shear viscosity measures the reaction to applied shear stress; and represents the ratio between the pressure exerted on the surface of a fluid, to the change in velocity of the fluid down the fluid. Shear viscosity is typically measured at an elevating shear rate, as exemplified in the Examples section that follows. Values are therefore indicated for a specific shear rate.

In some embodiments, the biocompatible polymer has a relatively low shear viscosity, particularly compared to hydrogels.

In some embodiments, a biocompatible polymer, although characterized as viscoelastic, does not form a hydrogel in an aqueous solution.

In some embodiments, the biocompatible polymer is water-soluble.

Selecting biocompatible polymers suitable for forming the hydrogel hybrids described herein should be evident to any person skilled in the art in view of the guidelines provided herein.

Exemplary biocompatible polymers that are suitable for use in the context of embodiments of the present invention are polysaccharides.

The term "polysaccharide" as used herein is meant to include compounds composed of 10 saccharide units and up to hundreds and even thousands of monosaccharide units per molecule, which are held together by glycoside bonds and range in their molecular weights from around 5,000 and up to millions of Daltons.

Polysaccharides that have desired physical properties, as defined herein with respect to swelling capability and viscoelasticity, are typically highly hydrated polysaccharides, or highly hydrated linear polysaccharides, as described hereinabove.

In some embodiments, the polysaccharide is a GAG. As noted hereinabove, GAGs are natural polymers which are major components of the native extracellular matrix (ECM), and are known to support enhanced cell attachment and proliferation.

In some embodiments, the polysaccharide is hyaluronic acid (HA).

In some embodiments, the polysaccharide is chitosan.

Additional suitable polysaccharides include, but are not limited to, agar, alginate, starch, laminarin and pectin, as long as these polymers exhibit the desired physical characteristics.

Additional exemplary suitable biocompatible polymers include, but are not limited to, proteins such as collagen, elastin and fibrin.

The biocompatible polymers can be a natural polymer or a synthetic polymer.

In some embodiments, the biocompatible polymer of choice has an average molecular weight that ranges from 1 kDa to 10,000 kDa. Without being bound by any particular theory, it is suggested that the molecular weight of the polymer affects the physical properties of the formed hybrid hydrogel, and can be selected so to impart the desired properties to the hydrogel.

For example, it is suggested that using polymers with higher molecular weight results in hybrid hydrogels with higher viscosity and vice versa.

In some embodiments, high molecular weight polymers, e.g., having a molecular weight higher than 10 kDa, are used.

In some embodiments, the hybrid hydrogel comprises more than one type of a biocompatible polymer as described herein.

Without being bound by any particular theory, the hybrid hydrogels described herein comprise fibrous networks which can be composed of peptide fibrils formed upon self-assembly of the peptides, with the biocompatible polymer being encaged therewithin, or, alternatively or in addition, can be composed of fibrous peptide structures having entangled therewith the polymer.

According to some embodiments of the present invention, the fibrils composing the hydrogel have an average diameter or a cross-section of less than 1 µm. In some embodiments, the fibrils have an average diameter that ranges from about 1 nm to about 500 nm, more preferably from about 10 nm to about 500 nm, more preferably from about 10 nm to about 200 nm and more preferably from about 10 nm to about 100 nm.

As used herein, the phrase "a plurality of peptides capable of self-assembling in an aqueous solution" encompasses any peptides that under certain conditions (e.g., concentration and/or temperature), spontaneously rearrange so as to form peptide fibrils that form the hydrogel's fibrous network.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to, N-terminus modification, C-terminus modification, peptide bond modification, including, but not limited to, $CH_2$—NH, CH—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Natural aromatic amino acids, Trp, Tyr and Phe, may be substituted for synthetic unnatural acids such as phenylglycine, TIC, naphthylalanine (Nal), ring-methylated derivatives of Phe, halogenated derivatives of Phe or O-methyl-Tyr, and β amino-acids.

In addition to the above, the peptides may also include one or more modified amino acids (e.g., biotinylated amino acids) or one or more non-amino acid monomers (e.g. fatty acids, complex carbohydrates etc).

As discussed hereinabove, it has been shown previously the relatively short aromatic peptides can self-assemble into hydrogels, presumably due to aromatic interactions.

In some embodiments, the peptides used for forming the hybrid hydrogels described herein have at least two amino acid residues and up to 6 amino acid residues, provided that at least one amino acid residue, in each peptide of the plurality of peptides used, is an aromatic amino acid. Thus, each of the peptides used for forming the hydrogels described herein can have two, three, four, five or six amino acid residues.

The peptides used for forming the hydrogels described herein are therefore relatively short peptides. Using such relatively short peptides is highly advantageous, allowing the formation of complex peptide nanostructures and fibrous networks from relatively cheap and readily available simple building blocks.

Each peptide in the plurality of peptides used for forming the hydrogel comprises at least one aromatic amino acid residue In some embodiments of the present invention, at least one peptide in the plurality of peptides used for forming the hydrogel is a polyaromatic peptide, comprising two or more aromatic amino acid residues. In some embodiments, at least one peptide in the plurality of peptides consists essentially of aromatic amino acid residues. In some embodiments, each peptide in the plurality of peptides consists essentially of aromatic amino acid residues.

Thus, for example, the peptides used for forming the hybrid hydrogel described herein can include any combination of: dipeptides composed of one or two aromatic amino acid residues; tripeptides including one, two or three aromatic amino acid residues; tetrapeptides including two, three or four aromatic amino acid residues; pentapeptides including two, three, four or five aromatic amino acid residues; and hexapeptides including two, three, four, five or six aromatic amino acid residues.

In some embodiments, one or more peptides in the plurality of peptides used for forming the hybrid hydrogel include two amino acid residues, and hence is a dipeptide.

In some embodiments, each of the peptides used for forming the hybrid hydrogel comprises two amino acid residues and therefore the hybrid hydrogel is formed from a plurality of dipeptides.

Each of these dipeptides can include one or two aromatic amino acid residues. Preferably, each of these dipeptides includes two aromatic amino acid residues. The aromatic residues composing the dipeptide can be the same, such that the dipeptide is a homodipeptide, or different. In some embodiments, the hydrogel is formed from homodipeptides.

Hence, in some embodiments of the present invention, each peptide in the plurality of peptides used for forming the hybrid hydrogel is a homodipeptide composed of two aromatic amino acid residues that are identical with respect to their side-chains residue.

The phrase "aromatic amino acid residue", as used herein, refers to an amino acid residue that has an aromatic moiety in its side-chain.

As used herein, the phrase "aromatic moiety" describes a monocyclic or polycyclic moiety having a completely conjugated pi-electron system. The aromatic moiety can be an all-carbon moiety or can include one or more heteroatoms such as, for example, nitrogen, sulfur or oxygen. The aromatic moiety can be substituted or unsubstituted, whereby when substituted, the substituent can be, for example, one or more of alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

Exemplary aromatic moieties include, but are not limited to, phenyl, biphenyl, naphthalenyl, phenanthrenyl, anthracenyl, [1,10]phenanthrolinyl, indoles, thiophenes, thiazoles and, [2,2']bipyridinyl, each being optionally substituted. Thus, representative examples of aromatic moieties that can serve as the side chain within the aromatic amino acid residues described herein include, without limitation, substituted or unsubstituted naphthalenyl, substituted or unsubstituted phenanthrenyl, substituted or unsubstituted anthracenyl, substituted or unsubstituted [1,10]phenanthrolinyl, substituted or unsubstituted [2,2']bipyridinyl, substituted or unsubstituted biphenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline, and purine.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "cycloalkyl" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydrofurane, tetrahydropyrane, morpholino and the like.

A "hydroxy" group refers to an —OH group.

A "thio" group (also referred to herein, interchangeably as "thiol" or "thiohydroxy") refers to a —SH group.

An "azide" group refers to a —N=N=N group.

An "alkoxy" group refers to both an —O-alkyl and an —O-cycloalkyl group, as defined herein.

An "aryloxy" group refers to both an —O-aryl and an —O-heteroaryl group, as defined herein.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" or "halide" group refers to fluorine, chlorine, bromine or iodine.

A "halophenyl" group refers to a phenyl substituted by two, three, four or five halo groups, as defined herein.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

The hydrogels of the present invention can be composed of linear or cyclic peptides (e.g., cyclic di-peptides of phenylalanine).

According to some embodiments of the present invention, one or more peptides in the plurality of peptides used to form the hydrogel described herein is an end-capping modified peptide.

The phrase "end-capping modified peptide", as used herein, refers to a peptide which has been modified at the N-(amine)terminus and/or at the C-(carboxyl)terminus thereof. The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

In a preferred embodiment of the present invention, all of the peptides that comprise the hydrogels are end-capping modified only at the N-termini.

However, other combinations of N-terminus end capping and C-terminus end capping of the various peptides composing the hydrogel are also contemplated. These include, for example, the presence of certain percents of end-capping modified peptides within the plurality of peptides, whereby the peptides are modified at the N-termini and/or the C-termini.

Another chemical property of an end-capping of a peptide is its hydrophobic/hydrophilic nature, which when unmodified, is hydrophilic in peptides. Altering the hydrophobic/hydrophilic property of one or both of the end-capping of the peptide may result, for example, in altering the morphology of the resulting fibrous network.

End-capping moieties can be further classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

Representative examples of aromatic end capping moieties suitable for N-terminus modification include, without limitation, fluorenylmethyloxycarbonyl (Fmoc). Representative examples of aromatic end capping moieties suitable for C-terminus modification include, without limitation, benzyl, benzyloxycarbonyl (Cbz), trityl and substituted trityl groups.

In some embodiments of the present invention, the end-capping modified peptides are modified by an aromatic (e.g. Fmoc) end-capping moiety. It is assumed that such an aromatic end-capping moiety also participates in the aromatic interactions, thus contributing to the formation and properties of the hybrid hydrogel.

The end-capping modified peptides utilized according to the present embodiments can be collectively represented by the following general Formula I:

$$R_1-[A_1]-[A_2]-\ldots[A_n]-R_2 \qquad \text{Formula I}$$

wherein:

n is an integer from 2 to 6;

$A_1, A_2, \ldots, A_n$ are each independently an amino acid residue as this term is defined herein, providing that at least one of $A_1, A_2, \ldots, A_n$ is an aromatic amino acid residue as this term is defined herein;

$R_1$ is an N-terminus end-capping moiety or absent; and $R_2$ is a C-terminus end-capping moiety or absent.

As described hereinabove, according to some embodiments of the present invention, the hydrogel comprises one or more end-capping modified homodipeptide.

Representative examples of end-capping modified homodipeptides include, without limitation, an end-capping modified naphthylalanine-naphthylalanine dipeptide, phenanthrenylalanine-phenanthrenylalanine dipeptide, anthracenylalanine-anthracenylalanine dipeptide, [1,10]phenanthrolinylalanine-[1,10]phenanthrolinylalanine dipeptide, [2,2']bipyridinylalanine-[2,2']bipyridinylalanine dipeptide, (pentahalo-phenylalanine)-(pentahalo-phenylalanine) dipeptide, phenylalanine-phenylalanine dipeptide, (aminophenylalanine)-(amino-phenylalanine) dipeptide, (dialkylamino-phenylalanine)-(dialkylamino-phenylalanine) dipeptide, (halophenylalanine)-(halophenylalanine) dipeptide, (alkoxy-phenylalanine)-(alkoxy-phenylalanine) dipeptide, (trihalomethyl-phenylalanine)-(trihalomethyl-phenylalanine) dipeptide, (4-phenyl-phenylalanine)-(4-phenyl-phenylalanine) dipeptide and (nitro-phenylalanine)-(nitrophenylalanine) dipeptide, whereby these homodipeptides are preferably end-capping modified by an aromatic moiety, and more preferably, are end-capping modified at the N-terminus thereof by an aromatic moiety such as Fmoc.

The end-capping modification of the peptides forming the hybrid hydrogel described herein can be further utilized for incorporating into the hydrogel a labeling moiety, as is detailed hereinbelow. Thus, according to an embodiment of the present invention, the one or more end-capping modified peptide comprises a labeling moiety. The labeling moiety can form a part of the end-capping moiety or can be the end-capping moiety itself.

In some embodiments of the present invention, the plurality of peptides in the hybrid hydrogel described herein comprises, or consists essentially of, a plurality of dipeptides, each comprising at least one aromatic amino acid residue.

In some embodiments, in each of the dipeptides both amino acid residues are aromatic amino acid residues, as described herein.

In some embodiments, in each of the dipeptides, the aromatic amino acid residues are the same, such that each of the dipeptides is a homodipeptide, or an aromatic homodipeptide.

In some embodiments, the plurality of dipeptides comprises, or consists essentially of, a plurality of Phe-Phe homodipeptides.

In some embodiments, the plurality of dipeptides comprises, or consists essentially of, a plurality of homodipeptides (e.g., Phe-Phe) which are end-capping modified peptides, wherein the end-capping moiety in such peptides in an aromatic moiety such as F-moc.

In some embodiments, the plurality of peptides comprises, or consists essentially of, a plurality of Fmoc-Phe-Phe (Fmoc-FF).

In some embodiments, the hydrogel comprises a fibrous network of a plurality of dipeptides, as described herein (e.g., Fmoc-FF), and hyaluronic acid.

In some embodiments, the hydrogel comprises a fibrous network of a plurality of dipeptides, as described herein (e.g., Fmoc-FF), and chitosan.

In some embodiments, the hydrogel comprises a fibrous network of a plurality of dipeptides, as described herein (e.g., Fmoc-FF), and any other biocompatible polymer, as described herein.

For each of hybrid hydrogels described herein, the total concentration of the peptide content (the plurality of peptides) and the biocompatible polymer ranges from 0.1 weight percent to 5 weight percents of the total weight of the gel, with the balance being water or an aqueous solution (e.g., a buffer).

Without being bound by any particular theory, it is suggested that at higher concentrations of the components forming the hydrogel, hydrogel with enhanced mechanical strength are obtained. On the other hand, too high concentrations of the components forming the hydrogel may interfere with the intermolecular interactions for forming the gel. This is more relevant to polymers with high molecular weight (such as HA). Thus, in case of polymers with molecular weight than is lower, for example, than 100 kDa, higher concentrations of the components can be used.

In some embodiments, the total concentration of the components ranges from 0.5 weight percent to 2.5 weight percent of the total weight of the gel.

In embodiments where the biocompatible polymer is hyaluronic acid, the total concentration of the peptide content (the plurality of peptides) and the biocompatible polymer ranges from 0.5 to 1 weight percent of the total weight of the gel.

In view of the surprising findings that the biological and physical properties of the hybrid hydrogels described herein are averagable, the ratio between the components in the gel also determines the properties of the obtained hybrid hydrogel and can be manipulated so as to control the physical and biological properties of the hybrid hydrogel.

In general, hybrid hydrogels with higher peptide content are characterized by higher storage shear modulus (G'), higher viscosity, lower elasticity and lower swelling ratio. Hybrid hydrogels with higher content of the biocompatible polymer are characterized by lower storage shear modulus (G'), lower viscosity, higher elasticity and higher swelling ratio.

The weight ratio of the dipeptides and the biocompatible polymer can range from 20:1 to 1:20, from 10:1 to 1:10, from 8:1 to 1:8, from 5:1 to 1:5, from 4:1 to 1:4, from 3:1 to 1:3, from 2:1 to 1:2 and can be 1:1.

In some embodiments, the weight ratio of the dipeptides and the biocompatible polymer is 1:1. In such hybrid hydrogels, the biological and physical properties are averaged between the components.

In some embodiments, the weight ratio of the dipeptides and the biocompatible polymer ranges from 3:1 to 1:3.

In exemplary embodiments, the total weight of the peptides and the polymer is 0.5 weight percent and the ratio between components ranges from 3:1 to 1:3.

As noted hereinabove, the hybrid hydrogels described herein can be regarded as means to enhance mechanical properties of biocompatible polymers, at one hand, and to improve biocompatibility and malleability of the peptide hydrogels, on the other hand.

Thus, in some embodiments, the hybrid hydrogel as described herein is characterized by a storage modulus G' to loss modulus G" ratio that is higher by at least 2-folds than such a ratio of a corresponding aqueous solution of the biocompatible polymer. By "corresponding aqueous solution" it is meant a solution with a concentration of the polymer or the peptides that is similar or the same as the total concentration of the polymer or the peptides in the hybrid hydrogel.

In many inert and living materials, the relationship between elastic and frictional stresses turns out to be very nearly invariant. The ratio between the elastic (storage) and frictional (loss) moduli is called the hysteresivity, h, or, equivalently, the structural damping coefficient. Thus, for each unit of peak elastic strain energy that is stored during a cyclic deformation, 10 to 20 percents of that elastic energy is taxed as friction and lost irreversibly to heat.

In systems conforming to the structural damping law, the hysteresivity h is constant with or insensitive to changes in oscillatory frequency, and the loss modulus G" becomes a constant fraction of the elastic modulus.

The hysteresivity represents the fraction of the elastic energy that is lost to heat, and is an intensive property that is dimensionless.

Higher storage to loss modulus ratio therefore indicates the formation of stronger and more rigid hydrogel.

In some embodiments, the hybrid hydrogel described herein is characterized by a shear storage modulus (G') that is lower by at least 10% of the storage modulus G' of a hydrogel formed from a corresponding aqueous solution of the plurality of peptides.

In some embodiments, the storage modulus of the hybrid hydrogel is lower by 10%, 20%, 30%, 40% and even 50% percents lower than the storage modulus of a hydrogel formed from a corresponding aqueous solution of the plurality of peptides.

Thus, the less rigid structure of the hybrid hydrogel compared to a corresponding hydrogel made from peptides without the polymer, advantageously renders the hybrid hydrogel malleable.

In some embodiments, the hybrid hydrogel described herein is characterized by a storage modulus G' that is higher by at least 5-folds of a storage modulus G' of a corresponding aqueous solution of the biocompatible polymer.

In some embodiments, the hybrid hydrogel is characterized by a storage modulus G' that is a 5-folds, 10-folds, 20-folds, 30-folds, 50-folds, 60-folds, 60-folds and even 100-folds higher than that of a corresponding aqueous solution of the biocompatible polymer.

The improved malleability of the hybrid hydrogels described herein is further demonstrated by its improved viscoelastic properties compared to each of the components when used alone in an aqueous solution.

In some embodiments, the hybrid hydrogel is characterized by a viscosity higher by at least 10% of a viscosity of the biocompatible polymer, when measured at an indicated shear rate.

Depending on the shear rate for a measured viscosity, the viscosity of the hybrid hydrogel can be higher by 10%, by 20%, by 50%, by 80%, or by 100% of that of a corresponding aqueous solution of the biocompatible polymer, and can be even 3-folds, 4-folds, 5-folds, 10-folds and even 100-folds or 1000-folds higher.

In some embodiments, the hybrid hydrogel is characterized by a viscosity change through time higher by at least 2-folds than a viscosity change through time of the biocompatible polymer, indicating less elasticity of the hybrid hydrogel compared to the biocompatible polymer.

In some embodiments, the hybrid hydrogel is characterized by viscosity recovery after shear that is at least 2-folds, or at least 3-folds, or at least 5-folds, or at least 10-folds, and can also be as high as 100-folds higher than that of a hydrogel formed from a corresponding aqueous solution of the peptides, indicating higher elasticity of hybrid hydrogel compared to a peptide hydrogel. Also here, the differences of viscosity recovery after shear are as determined for a viscosity measured certain shear rate.

In some embodiments, the hybrid hydrogel is characterized by a swelling ratio (Q) higher by at least 5%, or at least 10%, or at least 20%, or at least 50% of a swelling ratio of a hydrogel formed of a corresponding aqueous solution of the plurality of peptides. Higher swelling capability renders materials more suitable for biomaterial applications, as discussed hereinabove.

Indeed, in some embodiments, a hybrid hydrogel as described herein is characterized by biocompatibility to cell viability higher by at least 2-folds than a biocompatibility to cell viability of a hydrogel formed of the plurality of peptides.

By "biocompatibility to cell viability" it is meant the percents of cells that remain viable at an indicated time point post contacting the cells with the hydrogel, and is representing the suitability of the hybrid hydrogel as a matrix for cell growth.

In some embodiments, the hybrid hydrogel described herein is characterized as maintaining cells therewithin to an extent that is higher by at least 5%, at least 10%, at least 20%, at least 30% and even by at least 50% than that of a corresponding aqueous solution of the biocompatible polymer, indicating an improved capability of the hybrid hydrogel to serve as a scaffold, as defined herein, compared to the biocompatible polymer.

Further, as discussed hereinabove in the context of HA, biocompatible polymers are often biodegradable. Natural polymers are often further characterized by relatively fast biodegradation due to enzymatic degradation thereof. The fast biodegradation impediment the performance of such polymers in various applications.

As exemplified herein, biodegradation of such polymers is substantially reduced when combined into the hybrid hydrogels described herein.

Hence, in some embodiments, the hybrid hydrogels described herein are characterized by a biodegradation rate that is lower by at least 2-folds, at least 3-folds, at least 4-folds, at least 5-folds, at least 8-folds and even at least 10-folds or higher fold lower than the biodegradation rate of the biocompatible polymer.

Biodegradation rate can be determined by the time 50% of mass loss of a substance is observed; or, for example, by the degree of mass loss (e.g., as percentage of original mass) upon incubation for 7 days in a physiological medium.

By controllably averaging the biological and physical properties of its components, hybrid hydrogels as described herein feature such properties that are highly advantageous for biomaterial applications.

In some embodiments, a hybrid hydrogel as described herein is characterized by a storage modulus G' to loss modulus G" ratio that is greater than 1, greater than 2, greater than 3, greater than 4, and even greater than 5.

In some embodiments, a hybrid hydrogel as described herein is characterized by a storage modulus G' higher than 1,000 Pa at 10 Hz frequency and at 25° C.

In some embodiments, a hybrid hydrogel as described herein is characterized by a storage modulus G' lower than 100,000 Pa at 10 Hz frequency and at 25° C.

In some embodiments, a hybrid hydrogel as described herein is characterized by a viscosity that ranges from 200 to 2000 Pa·s at 0.1 $Sec^{-1}$ shear rate, at 25° C.

In some embodiments, a hybrid hydrogel as described herein is characterized by a viscosity change through time, as defined herein, higher than 1%, higher than 2%, and can be higher than 3% and even higher.

In some embodiments, a hybrid hydrogel as described herein is characterized by a viscosity recovery after shear that is at least 20%, at least 30%, at least 40% or at least 50% after 10 minutes at 0.1 sec$^{-1}$.

In some embodiments, a hybrid hydrogel as described herein is characterized by a swelling ratio (Q) that ranges from 100 to 500.

Notably, in some embodiments, the hybrid hydrogels described herein are devoid of a chemical cross-linking agent. Without being bound by any particular theory, it is suggested that the polymer and peptides are linked to one another in the hybrid hydrogel by a physical cross linking.

It should be noted that the structural, physical and chemical properties of the hybrid hydrogels described herein can be controlled and manipulated by employing different peptide building blocks, by altering the types of functional groups therein, and by varying the type of end-capping moiety used, and/or by employing different biocompatible polymers, and/or by altering their molecular weight, as well as by manipulating various parameters in their preparation (e.g., concentration of each component or total concentration of both components).

As demonstrated in the Examples section that follows, the hybrid hydrogels presented herein are formed in an aqueous solution that comprises the plurality of peptides and the biocompatible polymer.

Thus, according to another aspect of the present invention there is provided a process of preparing the hybrid hydrogels described herein. In some embodiments, the process is effected by contacting a plurality of peptides and the biocompatible polymer, as described in detail hereinabove, with an aqueous solution.

In some embodiments, the process is effected by dissolving the polymer in the aqueous solution and contacting the peptides with the aqueous solution in which the polymer is dissolved.

In some embodiments, the plurality of peptides is dissolved in a water-miscible solvent, prior to contacting the plurality of peptides with the polymer and the aqueous solution.

Contacting a solution of the peptides dissolved in an organic solvent with an aqueous solution comprising dissolved polymer can be regarded as diluting the peptide's solution to a concentration that allows self-assembly of the peptides.

The phrase "water-miscible organic solvent", as used herein, refers to organic solvents that are soluble in water. Several factors inherent in the structure of the solvent molecules can affect the miscibility of organic solvents in water, such as for example, the length of the carbon chain and the type of functional groups therein. Hydrogen bonding plays a key role in making organic solvents miscible in water. For example, in alcohols, the hydroxyl group can form hydrogen bonding with water molecules. In addition, aldehydes, ketones and carboxylic acids can form hydrogen bonding via the carbonyl oxygen. Hydrogen bonding between ether and water molecules is also possible, enabling some degree of miscibility of simple ethers in water.

Examples of water-miscible organic solvents include, without limitation, simple alcohols, such as, methanol, ethanol, 1-propanol, 2-propanol, 1-butanol, 2-butanol, 2-methyl-1-propanol, 2-methyl-2-propanol, 2,2-dimethyl-1-propanol and their halogen substituted analogues, ethylene glycol, acetone, dimethylsulfoxide, acetic acid diethyl ether, tetrahydrofuran etc.

Representative examples of organic solvents that were successfully practiced in generating exemplary hydrogels according to the present invention include, acetone, dimethylsulfoxide and hexafluoroisopropanol (e.g., 1,1,1,3,3,3-hexafluoro-2-propanol, abbreviated herein as HFIP).

In some embodiments, the organic solvent is dimethylsulfoxide (abbreviated DMSO).

As discussed hereinabove, the hydrogels' properties can be manipulated by controlling the concentration of each of the components; the peptides and the biocompatible polymer, individually and as a total concentration in the solution.

In some embodiments, the total concentration of the plurality of peptides and the polymer and in the aqueous solution ranges from about 0.1 mg/ml to about 50 mg/ml, or from 0.1 mg/ml to 25 mg/ml, or from 0.1 mg/ml to 10 mg/ml.

The final concentration of the plurality of peptide and of the biocompatible polymer in the aqueous solution and hence in the generated hybrid hydrogel can be readily determined by determining the concentration of each component in the aqueous solution.

For example, one can prepare a stock solution of the peptides in a water-miscible organic solvent or in a solvent mixture of such an organic solvent and water, in a certain concentration of the peptides, and a stock aqueous solution in which the polymer is dissolved in the same concentration of the polymer as for the peptide solution, and then mix the desired relative amounts of the solutions, so as to determine the ratio between the components in hybrid hydrogel. The concentration of each component in the solution will determine the final total concentration of the components in the hybrid hydrogel. Other manipulations of the concentration of each component in its stock solution and of the ratio between the stock solutions when contacted are also contemplated.

In some embodiments, the aqueous solution is a buffer (e.g., PBS).

The process of generating the hybrid hydrogels described hereinabove is preferably performed at room temperature. Alternatively, it can be effected at a physiological temperature (e.g., at 37° C.).

In some embodiments, contacting is further effected by mixing the formed aqueous solution (containing both components). Mixing can be performed, for example, by manual or mechanical shaking (e.g., by vortex), or by magnetic or mechanical stirring. In some embodiments, missing is performed by means of vortex.

Notably, the hybrid hydrogels described herein are generated without using a chemical crosslinking agent.

Once both the peptides and the polymer are contacted with an aqueous solution, and optionally the solution is mixed, a hydrogel is formed. In some embodiments, a hydrogel is formed upon maintaining the mixture at room temperature, for a time period that ranges from 1 minute to about 1 hour.

According to some embodiments of the present invention, the preparation of the hydrogel is effected prior to its application to a desired application site. Thus, for example, when the desired application site is a bodily organ or cavity, the hydrogel is prepared ex-vivo, prior to its application, by contacting the plurality of peptides, the polymer and an aqueous solution, as described hereinabove, and is administered subsequent to its formation.

Alternatively, the preparation of the hybrid hydrogel can also be performed upon its application, such that the plurality of peptides, the polymer and the aqueous solution are each applied separately to the desired site and the hybrid hydrogel is formed upon contacting the peptides, the polymer and the aqueous solution at the desired site of application. Thus, for example, contacting the peptides and the aqueous solution can be performed in vivo, such that the plurality of peptides, the polymer and the aqueous solution are separately administered.

In some embodiments, in vivo contacting is effected by contacting the peptides with an aqueous solution that comprises the polymer at the desired site of application.

According to these embodiments, the administration is preferably effected locally, into a defined bodily cavity or organ, where the plurality of peptides, the polymer and the aqueous solution become in contact while maintaining the desired ratio therebetween that would allow the formation of a hydrogel within the organ or cavity. As discussed hereinabove, the plurality of peptides can be utilized either per se, or, optionally and preferably, be dissolved in a water-miscible organic solvent, or any other suitable organic solvent, as described hereinabove.

Using such a route of preparing the hybrid hydrogel in vivo allows to beneficially utilize the formed hydrogel in biomaterial applications such as, for example, dental procedures, as a dental implant or filling material, cosmetic or cosmeceutical applications, tissue regeneration, implantation, and in would healing, as a wound dressing that is formed at a bleeding site, as is further detailed hereinbelow.

The formation of the hydrogel can similarly be effected at other sites of actions, other than a bodily organ or cavity, in which the hydrogel can be beneficially utilized, according to the desired application. Such applications include, for example, nanoelectro- or microelecto-mechanical systems (also known as NEMS or MEMS, respectively).

Thus, according to another aspect of some embodiments of the present invention there is provided a kit for forming the hybrid hydrogel described herein. In some embodiments, such a kit comprises a plurality of peptides, as described herein, and a biocompatible polymer, as described herein. In some embodiments, the kit further comprises an aqueous solution. In some embodiments, the peptides and the polymer are individually packaged within the kit. When the kit further comprises an aqueous solution, each of the aqueous solution, the polymer and the peptides can be individually packaged within the kit. Optionally, the peptides and the aqueous solution are individually packaged within the kit, and the polymer is dissolved in the aqueous solution. In some embodiments, the peptides are dissolved in a water-miscible organic solvent as described herein. In some embodiments, the peptide and the organic solvent are individually packaged within the kit.

In some embodiments, the plurality of peptides, the polymer and the optional aqueous solution and organic solvent are present within the kit in amounts that would allow generation of a hydrogel upon contacting thereof.

In some embodiments, the kit further comprises instructions for generating a desired hybrid hydrogel, either ex vivo or in vivo, as described herein. The kit may further comprise instructions, and optionally directives in the form of a table, how to use the components thereto to achieve a hybrid hydrogel with desired total concentration of its components and/or with desired ratio of the peptides and the polymer.

Such a kit can be utilized to prepare the hydrogel described herein at any of the desired site of actions (e.g., a bodily cavity or organ) described hereinabove.

The plurality of peptides in such a kit can be in a lyophilized form.

As used herein, the phrases "desired site of application" and "desired application site" describe a site in which application of the hybrid hydrogel described herein is beneficial, namely, in which the hydrogel can be beneficially utilized for therapeutic, diagnostic, cosmetic, cosmeceutical and/or mechanical applications, as described in detail hereinbelow.

Such a kit can further comprise an active agent, as is detailed hereinbelow, which is incorporated in or on the hydrogel, upon its formation, so as to form the composition-of-matter described herein.

The active agent can be individually packaged within the kit or can be packaged along with the plurality of peptides, or along with the polymer or along with the aqueous solution.

As is further demonstrated in the Examples section that follows, the hydrogels formed according to the present invention are characterized by exceptional material properties, which render them highly advantageous for use in applicative technologies.

Thus, for example, the hydrogels described herein are characterized by malleability, which allows utilizing both their relative rigidity and elasticity. In some embodiments, the hybrid hydrogels are injectable and therefore may be suitable for use in various medical and/or cosmetic applications, as further discussed hereinbelow.

In some embodiments, the hybrid hydrogels described herein can be utilized as a matrix for encapsulating therein or attaching thereto various agents. Indeed, it was shown that various substances can be embedded on and/or in the hydrogels. As demonstrated in the Examples section that follows, the hybrid hydrogels enable to entrap therein biological substances such as cells, allowing expansion and elongation of the cells within the hydrogel.

Hence, according to another aspect of the present invention there is provided a composition-of-matter, which comprises the hydrogel described herein and at least one agent being incorporated therein and/or thereon.

As used herein, the term "incorporated" encompasses attachment, encapsulation, embedding, and entanglement and like interactions of the active agent and the hybrid hydrogel, which can occur on a surface of the hydrogel, including outer surface or internal surface of the fibrous network.

Agents that can be beneficially embedded in or on, or attached to, the hydrogel include, for example, therapeutically active agents, diagnostic agents, biological substances and labeling moieties. More particular examples include, but are not limited to, drugs, cells, proteins, enzymes, hormones, growth factors, nucleic acids, organisms such as bacteria, fluorescence compounds or moieties, phosphorescence compounds or moieties, and radioactive compounds or moieties.

As used herein, the phrase "therapeutically active agent" describes a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), anti-psychotic agents, analgesics, anti-thrombogenic agents, anti-platelet agents, anti-coagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

As used herein, the phrase "biological substance" refers to a substance that is present in or is derived from a living organism or cell tissue. This phrase also encompasses the organisms, cells and tissues. Representative examples therefore include, without limitation, cells, amino acids, peptides, proteins, oligonucleotides, nucleic acids, genes, hormones, growth factors, enzymes, co-factors, antisenses, antibodies, antigens, vitamins, immunoglobulins, cytokines, prostaglandins, vitamins, toxins and the like, as well as organisms such as bacteria, viruses, fungi and the like.

As used herein, the phrase "diagnostic agent" describes an agent that upon administration exhibits a measurable feature that corresponds to a certain medical condition. These include, for example, labeling compounds or moieties, as is detailed hereinunder.

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent compounds or moieties, phosphorescent compounds or moieties, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

As used herein, the term "chromophore" refers to a chemical moiety or compound that when attached to a substance renders the latter colored and thus visible when various spectrophotometric measurements are applied.

A heavy metal cluster can be, for example, a cluster of gold atoms used, for example, for labeling in electron microscopy or X-ray imaging techniques.

As used herein, the phrase "fluorescent compound or moiety" refers to a compound or moiety that emits light at a specific wavelength during exposure to radiation from an external source.

As used herein, the phrase "phosphorescent compound or moiety" refers to a compound or moiety that emits light without appreciable heat or external excitation, as occurs for example during the slow oxidation of phosphorous.

As used herein, the phrase "radioactive compound or moiety" encompasses any chemical compound or moiety that includes one or more radioactive isotopes. A radioactive isotope is an element which emits radiation. Examples include $\alpha$-radiation emitters, $\beta$-radiation emitters or $\gamma$-radiation emitters.

While a labeling moiety can be attached to the hydrogel, in cases where the one or more of the peptides composing the hydrogel is an end-capping modified peptide, the end-capping moiety can serve as a labeling moiety per se.

Thus, for example, in cases where the Fmoc group described hereinabove is used as the end-capping moiety, the end-capping moiety itself is a fluorescent labeling moiety.

In another example, wherein the Fmoc described hereinabove further includes a radioactive fluoro atom (e.g., $^{18}F$) is used as the end-capping moiety, the end-capping moiety itself is a radioactive labeling moiety.

Other materials which may be incorporated in or on the hybrid hydrogel described herein include, without limitation, conducting materials, semiconducting materials, thermoelectric materials, magnetic materials, light-emitting materials, biominerals, polymers and organic materials.

Each of the agents described herein can be incorporated in or on the hydrogel by means of chemical and/or physical interactions. Thus, for example, compounds or moieties can be attached to the external and/or internal surface of the hydrogel, by interacting with functional groups present within the hydrogel via, e.g., covalent bonds, electrostatic interactions, hydrogen bonding, van der Waals interactions, donor-acceptor interactions, aromatic (e.g., $\pi$-$\pi$ interactions, cation-$\pi$ interactions and metal-ligand interactions. These interactions lead to the chemical attachment of the material to the fibrous network of the hybrid hydrogel.

As an example, various agents can be attached to the hydrogel via chemical interactions with the side chains, N-terminus or C-terminus of the peptides composing the hydrogel and/or with the end-capping moieties, if present.

Alternatively, various agents can be attached to the hydrogel by physical interactions such as magnetic interactions, surface adsorption, encapsulation, entrapment, entanglement and the like.

Attachment of the various agents to the hybrid hydrogel can be effected either prior to or subsequent to the hydrogel formation. Thus, for example, an agent or moiety can be attached to one or more of the peptides composing the hydrogel prior to the hydrogel formation, resulting in a hydrogel having the agent attached thereto. Alternatively, an agent or moiety can be attached to surface groups of the hydrogel upon its formation.

Incorporation of the various agents can be effected by forming the hybrid hydrogel in a solution containing the incorporated agent.

Hydrogels entrapping therein a biological or chemical agent can be beneficially utilized for encapsulation and controlled release of the agent.

Hydrogels having a labeling moiety attached thereto or encapsulated therein can be utilized in a variety of applications, including, for example, tracing and tracking the location of the fibrous networks of the present invention in mechanical devices and electronic circuitry; and tracing, tracking and diagnosing concentrations of the hybrid hydrogels of the present invention in a living tissue, cell or host.

As is further detailed in the Examples section that follows, it has been shown that the hydrogel described herein can be utilized as a highly efficient cell culture matrix, which maintains the cells viability, morphology and proliferation rate.

Hence, by being characterized by controllable, averagable biological and physical properties, the hybrid hydrogels and composition-of-matters described herein can be beneficially utilized in various applications, as is detailed hereinunder.

The hybrid hydrogels or composition-of-matters described herein can, for example, form a part of a pharmaceutical, cosmetic or cosmeceutical compositions, either alone or in the presence of a pharmaceutically or cosmetically acceptable carrier.

As used herein, a "pharmaceutical, cosmetic or cosmeceutical composition" refers to a preparation of the hydrogel or the composition-of-matter described herein, with other chemical components such as acceptable and suitable carriers and excipients. The purpose of a pharmaceutical composition is to facilitate administration of a compound to an organism. The purpose of a cosmetic or cosmeceutical composition is typically to facilitate the topical application of a compound to an organism, while often further providing the preparation with aesthetical properties.

Hereinafter, the term "pharmaceutically, cosmetically or cosmeceutically acceptable carrier" refers to a carrier or a diluent that does not cause significant irritation to an organism and does not abrogate the biological activity and properties of the applied compound. Examples, without limitations, of carriers include propylene glycol, saline, emulsions and mixtures of organic solvents with water, as well as solid (e.g., powdered) and gaseous carriers.

The compositions described herein may be formulated in conventional manner using one or more acceptable carriers comprising excipients and auxiliaries, which facilitate processing of the hydrogel into preparations. Proper formulation is dependent upon the route of administration chosen.

Techniques for formulation and administration of drugs may be found in "Remington's Pharmaceutical Sciences," Mack Publishing Co., Easton, Pa., latest edition.

The pharmaceutical compositions described herein can be formulated for various routes of administration. Suitable routes of administration may, for example, include oral, sublingual, inhalation, rectal, transmucosal, transdermal, intracavemosal, topical, intestinal or parenteral delivery, including intramuscular, subcutaneous and intramedullary injections as well as intrathecal, direct intraventricular, intravenous, intraperitoneal, intranasal, or intraocular injections.

Formulations for topical administration include but are not limited to lotions, ointments, gels, creams, suppositories, drops, liquids, sprays and powders. Conventional carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The compositions may, if desired, be presented in a pack or dispenser device, such as an FDA (the U.S. Food and Drug Administration) approved kit, which may contain the hydrogel. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert.

Additionally, in some embodiments, the hybrid hydrogels, composition-of-matters or compositions described herein can be utilized for forming an article-of-manufacture, whereby the article-of-manufacture can be, for example, a cell culture matrix, a protein microarray chip, a biosensor, a medicament, a drug delivery system, a cosmetic or cosmeceutical agent, an implant, an artificial body part, a tissue engineering and regeneration system, and a wound dressing, as well as various medical devices.

Herein, the phase "cell culture matrix" refers to biocompatible natural and synthetic matrix that can be used to create defined three-dimensional (3D) microenvironment which allows cell growth. The matrix optimally mimics the natural environment of the cells. Cell culture matrices are often used in tissue engineering.

As used herein, the phrase "protein microarray chip" refers to a solid base, e.g., pieces of glass, on which different molecules of protein have been affixed at separate locations in an ordered manner, thus forming a microscopic array. In general, microarray chips are measurement devices used in biomedical applications to determine the presence and/or amount of proteins in biological samples. Other applications include, for example, the identification of protein-protein interactions, of substrates of protein kinases, or of targets of biologically active small molecules. Another use is as a base for antibodies, where the antibodies are spotted onto the protein chip and used as capture molecules to detect proteins from cell lysate solutions. As will be familiar to one ordinarily skilled in the art, the formation of high-density protein chips to fully understand protein function had previously been a tremendous challenge. This is because proteins need to be in a wet environment in order to remain structurally intact and carry out their biological functions. Since hydrogels allow the proteins to remain in a wet environment as described hereinabove, it is highly advantageous to use hydrogels in forming protein microarray chips.

Herein the term "biosensor" refers to a device that combines a biological component with a physicochemical detector component and which is utilized for the detection of an analyte.

As used herein, the term "medicament" refers to a licensed drug taken to cure or reduce symptoms of an illness or medical condition.

As used herein, the phrase "drug delivery system" refers to a system for transportation of a substance or drug to a specific location, and more specifically, to a desired bodily target, whereby the target can be, for example, an organ, a tissue, a cell, or a cellular compartment such as the nucleus, the mitochondria, the cytoplasm, etc. This phrase also refers to a system for a controlled release of a substance or drug at a desired rate.

As used herein, the term "implant" refers to artificial devices or tissues which are made to replace and act as missing biological structures. These include, for example, dental implants, artificial body parts such as artificial blood vessels or nerve tissues, bone implants, and the like.

As used herein, the phrase "tissue engineering and regeneration" refers to the engineering and regeneration of new living tissues in vitro, which are widely used to replace diseased, traumatized or other unhealthy or unaesthetic tissues, collectively referred to herein as "damaged tissue".

As used herein, the phrase "cosmetic or cosmeceutical agent" refers to topical substances that are utilized for aesthetical purposes. Cosmeceutical agents typically include substances that further exhibit therapeutic activity so as to provide the desired aesthetical effect. Cosmetic or cosmeceutical agents in which the hydrogels, compositions-of-matter and compositions described herein can be beneficially utilized include, for example, agents for firming a defected skin or nail, make ups, gels, lacquers, eye shadows, lip glosses, lipsticks, and the like.

Medical devices in which the hydrogels, compositions-of-matter and compositions described herein can be beneficially utilized include, for example, anastomotic devices (e.g., stents), sleeves, films, adhesives, scaffolds and coatings.

Stents comprising the hydrogels, compositions-of-matter or compositions described herein can be used, for example, as scaffolds for intraluminal end to end anastomoses; as gastrointestinal anastomoses; in vascular surgery; in transplantations (heart, kidneys, pancreas, lungs); in pulmonary airways (trachea, lungs etc.); in laser bonding (replacing sutures, clips and glues) and as supporting stents for keeping body orifices open.

Sleeves comprising the hydrogels, compositions-of-matter or compositions described herein can be used, for example, as outside scaffolds for nerves and tendon anastomoses.

Films comprising the hydrogels, compositions-of-matter or compositions described herein can be used, for example, as wound dressing, substrates for cell culturing and as abdominal wall surgical reinforcement.

Coatings of medical devices comprising the hydrogels, compositions-of-matter or compositions described herein can be used to render the device biocompatible, having a therapeutic activity, a diagnostic activity, and the like.

Other devices include, for example, catheters, aortic aneurysm graft devices, a heart valve, indwelling arterial catheters, indwelling venous catheters, needles, threads, tubes, vascular clips, vascular sheaths and drug delivery ports.

Other potential non pharmaceutical applications of the hydrogel of the present invention are related to the exceptional material properties of the hydrogel. These applications include, for example, employing the hydrogel in a vibration-damping device or in a packaging material.

As used herein, the term "vibration-damping device" refers to a device which tends to reduce the amplitude of oscillations. Applications include for example the reduction of electric-signal (and hence sound) distortion in audio-electrical devices.

As used herein, the term "packaging material" refers to material designated for the enclosing of a physical object, typically a product which needs physical protection.

Due to the high biocompatibility of the hybrid hydrogels described herein, in particular cell viability-related biocompatibility, these hybrid hydrogels, or scaffolds made therefrom, can be used for inducing tissue formation, either in vivo or ex vivo.

Thus, in some embodiments, the hybrid hydrogels described herein, compositions-of-matter, compositions, kits or articles containing the same, can be used for inducing tissue formation or in the manufacture of a medicament or an agent for inducing tissue formation, either in vivo or ex vivo.

The phrase "in vivo" refers to within a living organism such as a plant or an animal, preferably in mammals, preferably, in human subjects.

In vivo induction of tissue formation can be made by administering the hydrogel hybrid or a composition-of-matter comprising the hybrid hydrogel, as described herein, to a desired sire of application, as defined herein.

In some embodiments, administering can be effected by injection or by other implanting (e.g., by using a scalpel, spoon, spatula, or other surgical device) the hydrogel at the desired site of application.

As used herein, the term "subject" refers to a vertebrate, preferably a mammal, more preferably a human being (male or female) at any age.

Optionally, in vivo induction of tissue formation can be made by administering to a subject the biocompatible hydrogel, the peptides and optionally an aqueous solution, as described hereinabove for regenerating the hybrid hydrogel at a desired site of application.

In some embodiments, in vivo induction of tissue formation can be effected by utilizing a composition-of-matter as described herein, which comprises the hybrid hydrogel as described herein and an active agent that is useful in promoting or inducing tissue formation. Exemplary such agents include, but are not limited to, growth factors, for example, insulin-like growth factor-1 (IGF-1), a transforming growth factor-β (TGF-β), a basic fibroblast growth factor (bFGF), a bone morphogenic protein (BMP), a cartilage-inducing factor-A, a cartilage-inducing factor-B, an osteoid-inducing factor, a collagen growth factor and osteogenin; and cells capable of promoting tissue formation, such as, but not limited to, stem cells such as embryonic stem cells, bone marrow stem cells, cord blood cells, mesenchymal stem cells, adult tissue stem cells, or differentiated cells such as neural cells, retina cells, epidermal cells, hepatocytes, fibroblasts, chondrocytes, pancreatic cells, osseous cells, cartilaginous cells, elastic cells, fibrous cells, myocytes, myocardial cells, endothelial cells, smooth muscle cells, and hematopoietic cells.

As used herein, the phrase "ex vivo" refers to living cells which are derived from an organism and are growing (or cultured) outside of the living organism, preferably, outside the body of a vertebrate, a mammal, or human being. For example, cells which are derived from a human being such as human muscle cells or human aortic endothelial cells and are cultured outside of the body are referred to as cells which are cultured ex vivo.

Ex vivo induction of tissue formation can be effected, according to some embodiments of the present invention, by seeding the hybrid hydrogel as described herein, or a composition-of-matter as described herein, with cells. Exemplary cells are as described hereinabove.

The phrase "tissue" refers to part of an organism consisting of an aggregate of cells having a similar structure and function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue and fat tissue. Preferably, the phrase "tissue" as used herein also encompasses the phrase "organ" which refers to a fully differentiated structural and functional unit in an animal that is specialized for some particular function. Non-limiting examples of organs include head, brain, eye, leg, hand, heart, liver kidney, lung, pancreas, ovary, testis, and stomach.

The term "seeding" refers to encapsulating, entrapping, plating, placing and/or dropping cells into the hybrid hydrogel (or composition-of-matter).

It will be appreciated that seeding the hybrid hydrogel with cells can be performed following the formation of the hydrogel or prior to hydrogel formation, i.e., by mixing the cells with the aqueous solution containing the peptides and the polymer, as described hereinabove for generating the hydrogel. The concentration of cells to be seeded on the hydrogels depends on the cell type and the hydrogel properties.

In some embodiments, following seeding the cells on the hydrogel, the cells are cultured in the presence of tissue culture medium and growth factors.

Thus, the hybrid hydrogels described herein can be formed in vitro, ex vivo or in vivo, and can be used to induce tissue formation and/or regeneration and thus treat individuals suffering from tissue damage or loss.

Thus, according to another aspect of some embodiments of the present invention there is provided a method of repairing a damaged tissue in a subject in need thereto. The method can be regarded as a method of treating a subject having a disorder characterized by tissue damage or loss.

Accordingly, the hybrid hydrogels described herein, compositions-of-matter, compositions, kits or articles containing the same, can be used for repairing a damaged tissue in a subject of for treating a subject having a disorder characterized by tissue damage or loss.

As used herein the phrase "disorder characterized by tissue damage or loss" refers to any disorder, disease or condition exhibiting a tissue damage (i.e., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration for medical or aesthetical purposes. Examples for disorders or conditions requiring tissue regeneration include, but are not limited to, liver cirrhosis such as in hepatitis C patients (liver), Type-1 diabetes (pancreas), cystic fibrosis (lung, liver, pancreas), bone cancer (bone), burn and wound repair (skin), age related macular degeneration (retina), myocardial infarction, myocardial repair, CNS lesions (myelin), articular cartilage defects (chondrocytes), bladder degeneration, intestinal degeneration, and the like.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

The method is effected by contacting the damaged tissue or an organ having tissue loss with the hydrogel as described herein or with a composition-of-matter as described herein or with a pharmaceutical, cosmetic or cosmeceutical composition, as described herein. Contacting can be effected by administering the hydrogel, composition-of-matter or composition to subject, preferably locally administering to the desired site of application (e.g., damaged tissue or organ with tissue loss), as described herein. Optionally, contacting is effected by contacting the desired site of application with the plurality of peptides and the biocompatible polymer, as described herein.

It will be appreciated that whenever a composition-of-matter as described herein comprises cells, the cells can be derived from the treated individual (autologous source) or from allogeneic sources such as embryonic stem cells which are not expected to induce an immunogenic reaction.

In some embodiments, treating the damaged tissue is effected by filling the gap of the defect by the hybrid hydrogel or composition as described herein, so as to initiate the regeneration of new cartilage tissue.

As noted hereinabove, in some embodiments, the methods and uses as described herein can be utilized for cosmetic or cosmeceutical applications, for example, for treating age-related damaged skin tissues (e.g., wrinkles), or trauma-related damages tissues, or for firming any other defected skin area, nail area or defected mucosal tissue.

It is expected that during the life of a patent maturing from this application many relevant biocompatible polymers and self-assembled peptides will be developed and the scope of the terms "biocompatible polymer" and "self-assembled peptide" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Hybrid Hydrogel Formation and Characterization
Materials and Experimental Methods
Materials:

Lyophilized Fmoc-diphenylalanine peptide was purchased from Bachem (Budendorf, Switzerland).

High molecular weight ($3\times10^6$) hyaluronic acid as a sodium salt was obtained from BTG-Ferring (Kyriat Malahy, Israel) in syringes as a solution of 1% HA in PBS.

Formation of Hybrid Fmoc-FF/HA Hydrogels:

In a typical procedure, lyophilized Fmoc-FF peptide was dissolved in DMSO (Dimethyl sulfoxide) to achieve a concentration of 0.1 mg/ml. The peptide stock solution was diluted by adding HA (1%) solubilized in $ddH_2O$ (DDW), to achieve a final concentration 0.5% w/w (5 mg/ml) of the combined substances. The mixture was physically blended by vortex and then maintained at room temperature until gelation is complete, unless otherwise indicated.

Different hybrid hydrogels were prepared by using different peptide-HA ratios. Thus, a 25/75 w/w hydrogel was composed of 1.25 mg Fmoc-FF and 3.75 mg HA in 1 ml solution. A 50/50 w/w hydrogel was composed of 2.5 mg Fmoc-FF and 2.5 mg HA in 1 ml solution. A 75/25 w/w hydrogel was composed of 3.75 mg Fmoc-FF and 1.25 mg HA in 1 ml solution.

To avoid any pre-aggregation and pre-assembly, fresh peptide stock solutions were prepared for each experiment.

Electronic Microscopy Measurements:

Three different electron microscopes have been used: TEM, SEM, and E-SEM, in order to cross-check and fully understand the morphological characterization of the newly formed hydrogels.

For TEM analysis, 100 μl samples of hydrogel were prepared and a portion of a sample was placed on a 400-mesh cupper grid. After 1 minute, the piece of gel was removed, as well as excess of fluid. Negative staining was obtained by covering the grid with 10 μl of 2% uranyl acetate in water. After 2 minutes, excess uranyl acetate solution was removed. Samples were viewed using a JEOL 1200EX electron microscope, operating at 80 kV.

For SEM analysis, fresh pieces of formed gel were placed on microscope glass cover slips and dried at room temperature, then spattered with gold. Images were obtained with a JSM JEOL 6300 scanning electron microscope operating at 5.0 kV.

E-SEM samples were prepared by placing pieces of gel on a microscope metal stand. Images were obtained using an FEI QUANTA 200 E-scanning electron microscope operating at 15.0 kV and with an FEI XL 30 E-scanning electron microscope field-emission gun at 5.0 kV and under reduced pressure of 2.5 Torr (1 Torr≈133 Pa).

Density:

Upon hydrogel formation, a pre-determined volume was collected by tips, and weighed, for specific density, calculating $gram/cm^3$. Hydrogels which were too rigid to be collected with a tip were cut with a scalpel to defined geometric shapes and the volume was calculated upon measuring the dimensions of these shapes.

Swelling:

Identical volumes of hydrogel samples were placed on plates, weights (Wi) were recorded, and the hydrogels were then placed in $ddH_2O$. To allow equilibration and swelling, all samples were allowed to swell for 24 hours. In 4 different time intervals through 2 weeks, the equilibrated swollen mass (Ws) have been recorded by gently absorbing excess of water from each sample. The hydrogel samples have been subsequently lyophilized and their dry weights (Wd) measured. The equilibrated swelling ratio (Q) was defined as the ratio of Ws to Wd.

Viscosity:

The apparent viscosity measurements of HA, Fmoc-FF and their hybrids were carried out using AR-G2 parallel plates rheometer (TA Instruments). Tests were carried out with a 20 mm plate at 25° C. and 37° C., applying a constant gap size of 1 mm Viscosity was measured using a stepped flow step program, at increasing shear rates, to evaluate non-Newtonian behavior of the hydrogels.

In addition, recovery after shear of the hydrogels was measured by comparing the viscosity at $t_0$ (which has undergone the above elaborated viscosity measurement test) to the viscosity of the same hydrogel after 10 minutes rest ($t_{10}$) at the same temperatures.

Rheological Studies:

The in-situ hydrogel formation, mechanical properties, and kinetics were characterized by an AR-G2 rheometer (TA Instruments). Time-sweep oscillatory tests in parallel-plate geometry were performed on 210 μl of fresh solution (resulting in a gap size of 0.6 mm) at room temperature. Oscillatory strain (0.01-100%) and frequency sweeps (0.01-100 Hz) were conducted in order to find the linear viscoelastic region, at which the time sweep oscillatory tests were performed. G', which represents the gel stiffness, was obtained at 10 Hz oscillation and 1% strain deformation for each sample was used to compare the relative mechanical stiffness of the hydrogels.

Results

Morphology Characterization:

The new hybrids include a natural component of HA and a synthetic component of Fmoc-FF.

FIG. 2 presents a photograph taken by a digital camera of hydrogels made of pure components and of various Fmoc-FF/HA weight ratios. As can be seen in FIG. 2, the macrostructure of all the different hydrogel hybrids exhibit a homogenous and transparent appearance. Upon comparisons between the different hybrids, it can be seen that in hydrogel with higher concentration of the peptide, the mechanical features are more pronounced and the hydrogels exert more brittle features, whereby in hydrogels made with higher concentration of HA, the hydrogel possesses a soft like fabric with a viscous behavior.

Under a centrifugation process, no segregation or phase separation occurs in any of the hydrogel preparations, suggesting that these constructs are homogenous biomaterials, well mixed, and blended. Moreover, two of the three hybrids (25/75, 50/50) were found suitable for injection through a thin needle, gyge of 21.

Figures 3A, 3B, 3C:
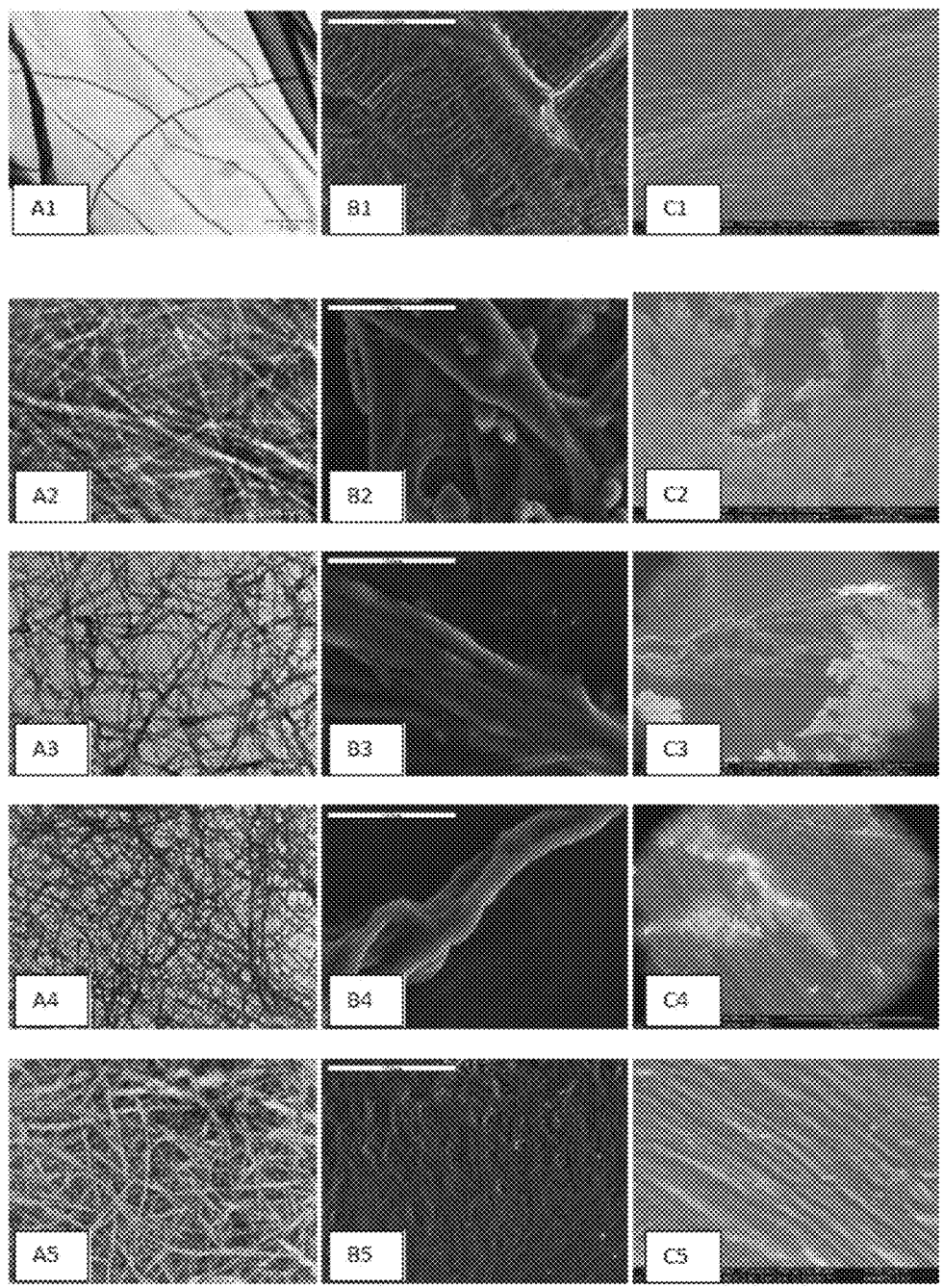

To gain more insight regarding the molecular organization of the self-assembled structures of Fmoc-FF and HA, TEM, SEM and E-SEM analyses were performed. The results, presented in FIGS. 3A-C, show that all hybrid hydrogels have a nature of fibrous networks (FIGS. 3A-C; (2), (3) and (4)), whereby higher concentrations of Fmoc-FF resulted in higher formation of tubular structures, and more dense structures. Hydrogel made of Fmoc-FF exhibited self-assembled tubular form (FIGS. 3A-C; (5)).

While all of the peptide-containing hydrogels form open-ended tubular structures, a remarkable size uniformity of the tubular structures' diameter was observed for all hydrogel's types, with the diameter being about 30-40 nm. However, the length of the tubular structures differs between the hydrogels. The hybrids Fmoc-FF/HA 25/75 and 50/50 have similar lengths ranging between 21±3 µm and 22±3 µm, respectively. The Fmoc-FF control hydrogel has a shorter length of 18±2 µm, while the hybrid Fmoc-FF/HA 75/25 has a surprisingly shorter length of only 11±2 µm.

It can be seen from the results that the hybrids Fmoc-FF/HA 25/75 and 50/50 are very much alike in their appearance and behavior, while the hybrid Fmoc-FF/HA 75/25 exhibits features that are more similar to the Fmoc-FF.

The E-SEM images (FIG. 3C (2), (3) and (4)) show a crystallized coating on top of the peptide nanotubes, seen as the brighter sections in these images. The crystallized coating is presumably formed of salts present in the PBS solution used for forming the hybrid hydrogels.

The time lapse to the crystallization appearance depends on the Fmoc-FF/HA ratio. In the 25/75 hybrid, crystallization occurs after 20 minutes at 5 Torr pressure and down to 3 Torr. In the 50/50 hybrid, it takes around 35 minutes under the same conditions. In the 75/25 hybrid, which is a denser hydrogel with many nanotubes and less HA, the crystallization lasts longer than 45 minutes. These data may suggest that HA is caged within the peptidic structure, such that in denser structures, with less HA, less crystallization is observed.

Figure 4:
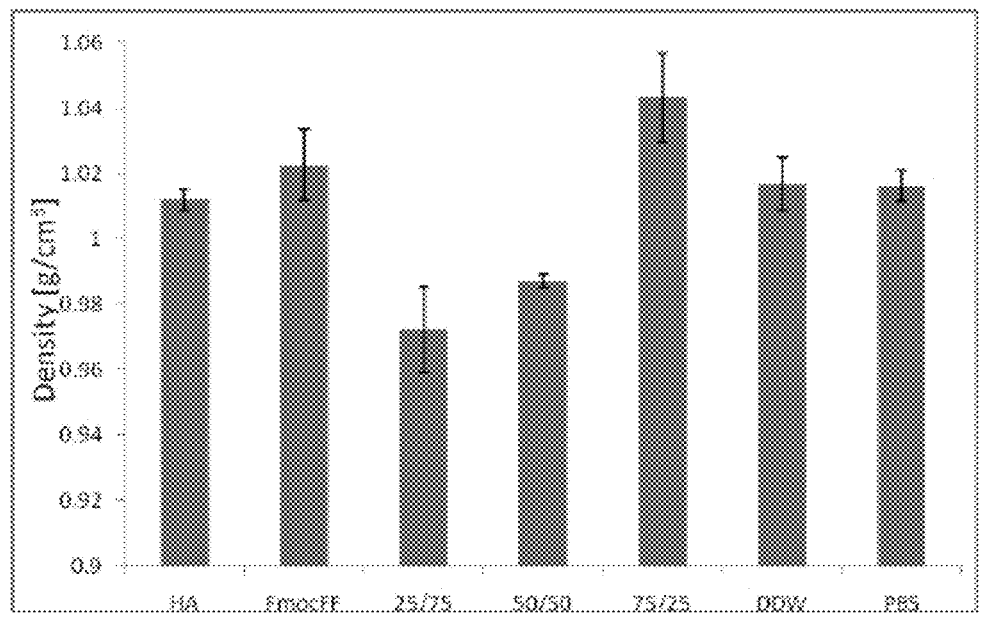
FIG. 4 is a bar graph presenting the density values calculated for solutions (DDW and PBS) and hydrogels made of pure components (Fmoc-FF and HA) and of hybrid hydrogels made from different weight ratios of Fmoc-FF/HA (n=3-6)

Density:

FIG. 4 presents the values calculated for the density of the various hydrogels obtained. As can be seen in FIG. 4, density measurements further suggest that the hybrid hydrogel made from 75/25 Fmoc-FF/HA has different features than the other tested hybrids (25/75 and 50/50 Fmoc-FF/HA).

Without being bound to any particular theory, it is assumed that combining HA with Fmoc-FF results in moderate hybrids that have averaged features. The original HA solution and Fmoc-FF have a similar density of about 1.012 and 1.022 gram/cm$^3$, respectively, which is close to the DDW and PBS density (1.016 g/cm$^3$). The hybrids 25/75 and 50/50 Fmoc-FF/HA have lower densities of 0.972 and 0.987 g/cm$^3$, respectively, which can be explained by the interference of the viscous HA molecules within the creation and organization of the Fmoc-FF nanotubes. It is to be noted that both HA and Fmoc-FF are negatively charged in aqueous solution at pH 7, and thus may experience electrostatic repulsion therebetween. In addition, HA molecules are hydrated, and thus present a hydrophilic nature, while the Fmoc-FF has a hydrophobic nature, due to its aromatic rings.

Along this line, the more Fmoc-FF is in the hydrogel, the denser the structure should be, as is indeed shown in FIG. 4.

The length of the formed tubular structures may also affect the final density, as shown for the two hybrids hydrogels made of 25/75 and 50/50 Fmoc-FF/HA, which were found to have the longest structures, as discussed hereinabove, and lower densities. Longer tubes are assumed to cause a less compact organization. The Fmoc-FF hydrogel has shorter nanotubes, resulting in a denser hydrogel.

This may also explain the higher density of the 75/25 Fmoc-FF/HA hybrid hydrogel, which was found to have the shortest nanotubes, as described hereinabove.

Because all hydrogels have the same dry weight (5 mg/ml), density represents the average pore size within the network, the pore size distribution, and the pore interconnections, which are features of a hydrogel matrix. These features of the porous structure determine the absorption (or partitioning) and diffusion of solutes through the hydrogel [A. S. Hoffman 2002 *Advanced Drug Delivery Reviews* 54(1): 3-12].

Swelling:

The character of the water in a hydrogel can determine the overall permeation of nutrients into, and cellular products out of, the gel [Hoffman 2002, supra]. The swelling ratio of the initial state of all of the hydrogels can be calculated from the hydrogel concentration used, 0.5%, which means 5 mg dry weight (Wd) in a total of 1000 µl (or 1000 mg) swelling weight (Ws). Dividing Ws by Wd resulted in a swelling ratio of 200 at the initial state (see, FIG. 5).

HA has a swelling capacity of 1000, as taken from the literature [Balazs, E. A. In *Chemistry and biology of hyaluronan*; Garg, H. G., C. A. Hales, C. A., Eds.; Elsevier ltd. 2004, Chapter 20], which represents its high hydration rate. The open, random coil structure of hyaluronic acid exhibits large solvent domains due to the large number of hydrophilic residues. This gives hyaluronic acid, even at low concentrations, the character of a high viscosity solution, which is responsible for its outstanding lubrication properties. However, this fact is of a great disadvantage as HA immediately disappears in aqueous environment and does not retain its structure.

Figure 5:
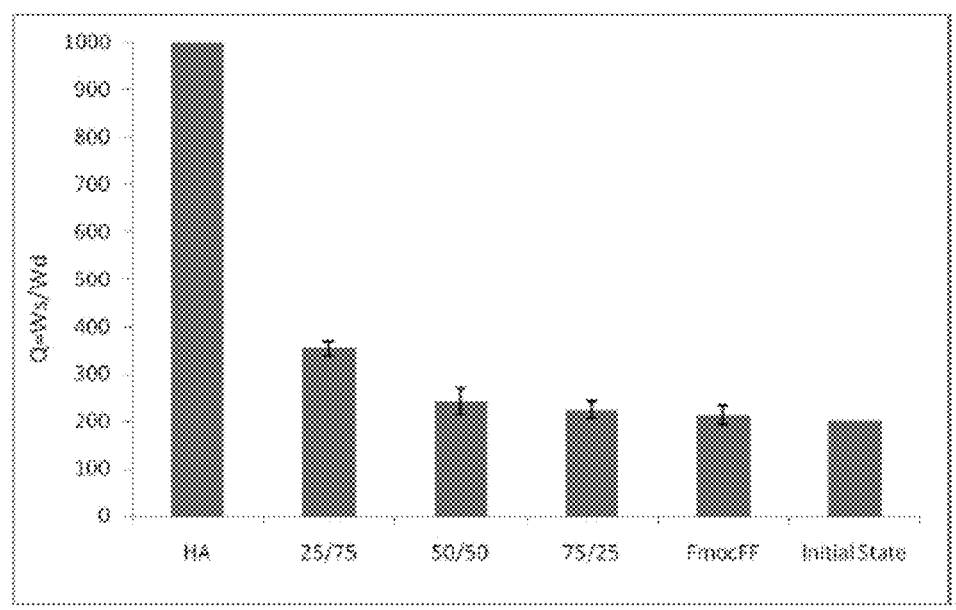
FIG. 5 is a bar graph presenting the swelling ratio calculated for hydrogels made of pure components (Fmoc-FF and HA) and of hybrid hydrogels made from different weight ratios of Fmoc-FF/HA, as an average of values obtained for 3 hydrogels of each hydrogel type at 4 time points during 2 weeks.

As shown in FIG. 5, the Fmoc-FF hydrogel has a swelling ratio of 212, similar to the initial state, which can be explained by its hydrophobic nature and hence its poor hydration ability.

As further shown in FIG. 5, all hybrid Fmoc-FF/HA hydrogels retained their structure even after 2 weeks in aqueous environment, and exhibited a swelling ratio averaging between the Fmoc-FF hydrogel and the HA. It can be seen that the higher the concentration of the peptide, the less swelling is attained.

It is noted that the hybrid hydrogel made of 75/25 Fmoc-FF/HA, which represents a denser state than the Fmoc-FF hydrogel, as discussed hereinabove, has a swelling ratio higher than that of the Fmoc-FF hydrogel (224 and 212, respectively). In addition, it is noted that although HA solution and Fmoc-FF hydrogel have almost the same density, their swelling properties are very diverse. Without being bound to any particular theory, it is suggested that the swelling ratio is affected by the elasticity of the chains composing the hydrogel. HA chains are very elastic and flexible, and can be pushed by water (and cells) while passing thereby. However, Fmoc-FF forms a dense network of tubular nanostructures through which water passing is limited. It is therefore suggested that the main factor affecting the swelling ratio is not the density of the solution, but the amount of the hydrophilic, flexible chains, of the HA, which have a high hydration rate and can be pushed by molecules passing therethrough.

Viscosity:

In order to explore the mechanical features of the hydrogels, the viscosity of the different hybrids was analyzed and compared to the control hydrogels—HA and Fmoc-FF (FIG. 6). All gels show the same behavior, where as the shear rate increases, the viscosity decreases. The viscosity was studied at 25° C. and 37° C. Very similar trends were exhibited at 37° C., with a reduction in viscosity at 37° C. in comparison with the 25° C. values, as expected. The higher the temperature, the solutions exhibit a more liquid nature and less flow resistance, expressing lower viscosity.

HA is known as a very viscoelastic solution [Coviello, T.; Matricardi, P.; Marianecci, C.; Alhaique, F. *J Control. Rel.* 2007, 119(1), 5-24]. At low shear rates the viscosity of a 1% HA solution is 150 Pa·s and it decreases moderately with the increase in shear rate (FIG. 6). HA also shows a high viscosity recovery tendency, with almost no change in viscosity between the two time intervals tested ($t_0$ and $t_{10}$). The high viscosity recovery of HA is supported, for example, in FIG. 6, where it is shown that shear rates minimally affect the viscosity of HA.

Fmoc-FF hydrogel (0.5%) exhibits a very high viscosity value of more than $5 \times 10^5$ Pa·s at low shear rates, showing a sharp decrease with increasing shear rates, due to the brittle nature of this hydrogel. In contrast to HA, Fmoc-FF shows low recovery after shear, as it exhibits lower values of viscosity upon measurement after 10 minutes rest (FIG. 7). The viscosity change between $t_0$ (viscosity at initial time) and $t_{10}$ (viscosity after 10 minutes rest) is indicative of the elasticity of the solution. Thus, the less change in the viscosity, the more elastic is the hydrogel.

All three hybrids show average levels of viscosity, between HA and Fmoc-FF. It can be seen that as the concentration of Fmoc-FF in the hydrogel hybrid is higher, the viscosity is higher (FIG. 6), and the recovery is lower (FIG. 7).

All three hybrids are composed of HA, which is a very viscoelastic solution, and Fmoc-FF, which is a very rigid but brittle hydrogel, therefore not showing full recovery after shearing. The hybrids 25/75 and 50/50 show very similar viscosity values with no significant difference, which can be explained by the morphological features of these hydrogels, as discussed hereinabove. The hybrid 75/25 shows values which resemble more the Fmoc-FF hydrogel, as can be also explained by its morphological features discussed supra.

In exemplary data obtained while measuring viscosity recovery after shear, it was shown that at shear rate of 0.1 $sec^{-1}$ the viscosity of a 50/50 Fmoc-FF/HA hybrid hydrogel was 573.7 Pa·s and after 10 minutes 325.8 Pa·s, representing 56% recovery.

The viscosity of Fmoc-FF hydrogel at the same shear rate was 2,038 Pa·s and after 10 minutes only 68 Pa·s, representing 3.3% recovery. At a shear rate of 1 $sec^{-1}$, the 50/50 Fmoc-FF/HA has a viscosity at t=0 of 23.43 Pa·s and at t=10 minutes 18 Pa·s, representing 76.8% recovery. Under the same shear rate, a Fmoc-FF hydrogel has at t=0 viscosity of 29.83 Pa·s and at t=10 minutes 10.59 Pa·s, representing a recovery of 35.5%.

Rheological Study:

The mechanical properties of the hydrogels can be used to determine their suitability to various applications. Hence, rheological characterization was conducted in order to study the kinetics of the hydrogel formation and the viscoelastic properties of the materials.

The complex shear modulus (G*) of the hydrogels showed that the elastic response component (G', storage modulus) exceeded the viscous response component (G", loss modulus, not shown) by at least an order of magnitude, indicating that a phase transition into a viscoelastic material occurred.

As can be seen in FIGS. 8-10, the different hydrogels exhibited different G' values and different kinetics of hydrogel formation. Rheological behavior was affected by both hydrogel's composition (FIG. 8), hydrogel's concentration (FIG. 9), and temperature (FIG. 10), as discussed in further detail hereinunder.

The obtained data is summarized in Table 1 below.

TABLE 1

| Hydrogel type & final concentration [%] | 4° C. G' [Pa] after 40 min | 25° C. G' [Pa] | 25° C. Gelation time [min] | 37° C. G' [Pa] | 37° C. Gelation time [min] |
|---|---|---|---|---|---|
| HA 1 | 162 | 158 | — | 135 | — |
| FmocFF 0.5 | 963 | 8767 | 10.5 | 9564 | 8.3 |
| FmocFF 1 | — | 122700 | 13.5 | 60770 | 7 |
| 25/75 0.5 | 524 | 1158 | 78 | 1227 | 17 |
| 50/50 0.5 | 1474 | 2076 | 16.5 | 1951 | 5.5 |
| 50/50 1 | — | 5030 | 18 | 4658 | 8.3 |
| 75/25 0.5 | 14860 | 25730 | 5.5 | 19000 | 1.2 |
| 75/25 1 | — | 85700 | 6 | 52020 | 2.5 |

FIG. 8 presents the values obtained for the storage shear modulus (G') as a function of time, for different hybrid hydrogels and for Fmoc-FF hydrogel at a concentration of 0.5% (5 mg/cc), and of an HA solution at 1%. The gelation time is determined by the time to reach its plateau, or the time the highest G' is achieved, and is indicative of the time requested for the tubular structures to arrange within the hydrogel. HA 0.5% hydrogel demonstrates G" values higher than G' values, which are typically indicative for liquid solutions. HA at 1% demonstrates G' four times higher than G" (178 and 46 Pa, respectively). The measured G' value is very low when compared to the other tested hydrogels, and is indicative for the softness of HA. The Fmoc-FF hydrogel demonstrates a very rigid biomaterial, with a G' of almost 9000 Pa and a gelation time of 10 minutes.

The hybrids 25/75 and 50/50 Fmoc-FF/HA demonstrate an averaged G', as expected, with very similar values of around 1200 Pa. Interestingly, similar rigidity was observed for these two hydrogel types, although different amounts of Fmoc-FF were used and thus the extent of tubular structures formation is different. These two hybrid hydrogel differ is the gelation time, which was longer in the 25/75 Fmoc-FF/HA hybrid.

The hybrid 75/25 Fmoc-FF/HA hydrogel was found to exhibit high rigidity of more than 25000 Pa and the lowest gelation time of only 5 minutes. These results are in accordance with the short nanotubes length of this hydrogel type, described hereinabove.

FIG. 9 presents the effect of hydrogel concentration (0.5% or 1%) on the rigidity, as measured at 25° C. As can be seen in FIG. 9 and Table 1, all hydrogels exhibited similar kinetic pattern with lower G' values as the concentration decreased. When concentration decreases in half (from 1% to 0.5%), G' values decrease more than 3 times, while the gelation time stays the same.

However, as can be seen in FIG. 10, various kinetic patterns were observed at different temperatures (for the same concentration of the 50/50 Fmoc-FF/HA hybrid hydrogel, as a representative example). The obtained data indicate that in hydrogels exhibiting lower G' values (less than 5000 Pa) temperature change from 25° C. to 37° C. has less significant effect on the G' value, yet affects the gelation time, probably due to faster self-assembly at higher temperatures.

As shown in Table 1, more rigid hydrogels (G' more than 5000 Pa) exhibit not only a change in the gelation time, but also a significant change in the G' values as a result of temperature change. The more Fmoc-FF in the hydrogel, the more dramatically the elastic properties (G') change at high temperature.

The temperature effects can be explained by self-assembly velocities, whereby at higher temperature, faster self-assembly results in reduced formation of nanotubes.

Example 2

Degradation of Hybrid Gels

Hydrogels' biodegradation was examined in the presence of hyaluronidase, an enzyme that degrades hyaluronic acid. The hybrid hydrogels described herein are designed so as to result in a slower degradation rate and longer retention time in the body, compared to that of HA, yet without using chemical cross-linking.

Assay Protocol:

The in vitro enzymatic degradations of the hydrogels were measured as a function of time by incubating the gels in the presence of hyaluronidase (Hyase), by monitoring the residual mass of the hydrogel; and by determining the released glucuronic acid from the hydrogel to the solution by a Dische assay, as described in [Z. Dische 1947 *J. Biol. Chem.* 167: 189-198]. In brief, 0.2 ml of 0.1% carbazole solution in alcohol was added to 1 ml of a tested sample. After vortexing, 6 ml of concentrated $H_2SO_4$ was added to the solution. The glass tubes were closed with coupled sleeves, boiled for 15 minutes in a water bath, and the solution was then chilled to room temperature and the absorption ($\lambda$=527 nm, colored pink—violet) was measured relatively to the blank reference solution.

Bovine testicular hyaluronidase, Type IV-S, as lyophilized powder (451 U/mg) was purchased from Sigma Aldrich (Rehovot, Israel).

One ml of each hydrogel was transferred into custom-made plastic tubes with 40 µm filter paper placed on the bottom. The tubes with the hydrogels were placed in glasses soaked with buffer (0.1 M monosodium phosphate in 0.15 M NaCl (pH 5.3)). Enzyme concentration of 10 U/ml buffer was chosen to imitate by approximation the endogenous enzyme levels. Enzyme concentrations of 1.25 U/ml, 2.5 U/ml, 3.75 U/ml were used for the 75/25, 50/50 and 25/75 Fmoc-FF/HA hydrogels, respectively, in order to match the amount of HA in the hydrogel to the enzyme concentration.

The hyaluronic acid release is uniaxial, taking place only at the interface of the hydrogel and buffer.

The gels were incubated for various time intervals at 37° C. with mild mixing on a platform shaker (50 rpm), for a week. At each time point, the solution was removed to determine the residual HA quantity by Dische's assay, as described hereinabove, and the residual gels' masses. The tubes were then returned to their glasses and replenished with fresh Hyase buffer solution for the remaining residues. Pure hyaluronic acid solution and Fmoc-FF hydrogel were used as a positive and negative control, respectively.

Results:

FIG. 11 presents the hydrogel's mass loss during the assay period (one week) upon incubating the tested hydrogels in the presence or absence of hyaluronidase. As shown in FIG. 11, substantially lower degradation was observed for hybrid hydrogels as compared to HA solution, with degradation extending from a few hours for the HA solution to 7 days. The enzyme concentration used has not affected the degradation rate (data not shown).

The obtained results suggest that enzyme penetration through the hybrid hydrogel network is limited, such that HA disappearance occurs as a result of its migration out of the hybrid complex. These data are in corroboration with the results obtained in the swelling assay.

FIG. 12 presents the data obtained for the release of glucuronic acid (as a result of HA enzymatic degradation) into the tested solution, which are in corroboration with the mass loss data. The hybrid 50/50 Fmoc-FF/HA hydrogel showed similar behavior in the presence and absence of the enzyme, again probably due to the poor penetration ability of the enzyme into the hydrogel. The hybrid 25/75 Fmoc-FF/HA hydrogel, which was found to exhibit higher swelling ability, exhibits higher extent of HA degradation.

Example 3

Biocompatability Assays

Cells Viability Test:

To verify the ability of the hybrid hydrogels described herein to be used in biological applications, their biocompatibility was determined using an in vitro cell culture experiment. Three types of cells were cultivated on top of the hybrid hydrogels: CHO (Chinese Hamster Ovaries), fibroblasts and chondrocytes.

Assay Protocol:

CHO, fibroblasts and chondrocytes cells were grown in Dulbecco's Modified Eagle Medium (DMEM) supplemented with 10% fetal calf serum, 100 U/ml penicillin, 100 U/ml streptomycin, and 2 mmol/liter L-glutamine (all from Beit Haemeck, Israel). Cells were maintained at 37° C. in a humidified atmosphere containing 5% $CO_2$. Subconfluent cultures were harvested by trypsinization, counted, and diluted in specific cells' media to form a cell concentration of $10^6$ cells/ml. The gels swelled overnight with 0.1 ml DMEM. The next day, DMEM was removed and 0.1 µl of the CHO cells ($10^5$ cells) were placed on top of the hydrogel. After 1, 3, and 7 days of incubation at 37° C. the viability of the cells was determined using an MTT assay.

Results:

The cell viability was analyzed 1, 3, and 7 days post seeding. Cells seeded as monolayers with PBS were used as control. Cell viability was analyzed using an MTT assay. When MTT was added to the cell culture medium, the mitochondrial dehydrogenase enzyme, which is present only in live cells, changed the color of the yellow MTT to dark-blue crystals, which accumulated inside the living cells and give a clear indication of cell viability.

As can be seen in FIG. 13, after 1 day, the cultured CHO cells showed high viability on both HA and the hybrid hydrogels. Cells on Fmoc-FF hydrogel showed lower viability of 50%. The viability of CHO cells on all hybrid hydrogels increased with time, whereas a moderated decrease in cell viability was recorded for the Fmoc-FF hydrogel.

In the other cell types tested, normal human fibroblasts and chondrocytes, a viability of about 80% was measured on the first day, for all hybrid hydrogels (data not shown). Without being bound to any particular theory, it is assumed that since these cells are primary cells, their sensitivity is higher than that of the CHO cell line. It is further assumed that the viability of primary cells is influenced from the Fmoc-FF/HA ratio in the hydrogel. As discussed hereinabove, it is assumed that the results are influenced by the permeation properties of the hydrogel, which limit the diffusion rate of the medium through the hydrogel, and may also affect the diffusion of the MTT reagent.

FIG. 14 represents an image of chondrocytes seeded on the hybrid 50/50 Fmoc-FF/HA hydrogel, showing that cell survived, and that their characteristic polygonal phenotype shape was captured.

Cell Dispersion:

Assay Protocol:

After mixing the components forming the hydrogel hybrids (immediately after vortex), 50 µl of each mixture was placed in a different well in a 96-well plate. HA solution and Fmoc-FF hydrogel were used as controls. Once gel formation was observed (for hybrid hydrogels and Fmoc-FF), 100 µl of DMEM was added to each well and the plate was placed in an incubator for overnight. Then, the medium was removed and $2.5 \times 10^4$ MSC (mesenchymal stem cells) ATCC in 100 µl fresh medium was seeded on top of each solution or hydrogel. Additional 100 µl DMEM was added, and the plate was incubated. After 2, 6 and 10 days of incubation, cell quantity was measured with a hemocytometer. A distinction between cells grown on the bulk gel or on the plate underneath was made by separately collecting medium & gel and then collecting the cells which grow on the plate by trypsinization.

Results:

FIGS. 15A-B present the data obtained for percents of cells found in medium and gel out of the total cell amount at different time points (FIG. 15A), and for percents of cells found grown on the plate out of the total cell amount at different time points.

It can be seen that cell proliferation in HA solution is very similar to plain plate. Even after 2 days, almost all the cells slipped down and grown on the plate. On the other hand, with the hydrogel hybrids, the cells remained in the gel even after 10 days. These remarkable results demonstrate the capability of the hybrid hydrogels to serve as an efficient scaffold for cells, a capability imparted by the enhanced rigidity of the hybrid hydrogels as compared with HA viscous solutions.

Example 4

In Ovo CAM Assay

Assay Protocol:

Chicken eggs in the early phase of breeding are between in vitro and in vivo systems and provide a vascular test environment to study toxicity of biomaterials, especially hydrogels. After the chick chorioallantoic membrane (CAM) has developed, its blood vessel network can be easily accessed, manipulated and observed and therefore provides an optimal setting for allo- and xenografts.

For experimental purposes, the tested substances are placed on the vasculature network of capillaries of the CAM of fertilized chicken eggs, upon 8 days in gestation. Detailed methods of CAM assays are described in Dohle et al. *J Vis Exp*. 2009 Nov. 30;(33).

In brief, exogenous limb-buds of a 4-day fertilized chicken egg were added to the tested Fmoc-FF/HA hybrid hydrogels. In embryology, limb bud is a structure formed by the developing limb. At day 4-4.5 to gestation (stage 24), the limb bud is full of MSCs (mesenchymal stem cells), which are multipotent stem cells that can differentiate into a variety of cell types, including: osteoblasts (bone cells), chondrocytes (cartilage cells) and adipocytes (fat cells).

The limb bud embedded in the hydrogel was placed on an 8-day fertilized egg (CAM), and after 6 days, the obtained tissue was removed and subjected to histology evaluation.

Results:

FIGS. 16A-C present light micrographs of H&E staining of limb-buds embedded in 50/50 Fmoc-FF/HA hybrid hydrogel after 6 days on a CAM of an 8-day fertilized chicken egg (X 25). FIG. 16A presents an initial stage of limb-bud; FIG. 16B presents chondrocytes condensation; and FIG. 16C presents organogenesis into limb formation.

As can be seen, the 50/50 hybrid hydrogel can mimic the stages of developmental limb, as occurs in embryology: first is the chondrocyte condensation into islands, as can be seen in FIG. 16B, and later is the limb formation (FIG. 16C). The MSCs not only survive on the 50/50 hydrogel, but also proliferate and differentiate into a limb, thus demonstrating the improved and potent biocompatibility of the hybrid hydrogels described herein.

Example 5

Formation of Hydrogel Hybrids Made of Chitosan and Self-Assembling Peptides

Materials and Methods

Chitosan having MW of 64000 Da was obtained from Koyo chemical CO., Ltd., Japan.

A 2% solution (20 mg/ml) of chitosan in acetic acid (0.25N) was prepared and after one day was titrated with NaOH 0.1N in order to achieve pH 6.9. A 0.1 mg/ml solution of Fmoc-FF in DMSO was thereafter added to the chitosan solution, the mixture was vortexed and maintained at room temperature until gel formation was observed. The amount of Fmoc-FF in the final mixture was 0.5 mg or 2 mg.

Thus, 2 µl or 5 µl of the peptide stock solution (0.2 mg or 0.5 mg Fmoc-FF, respectively) was added to the chitosan solution to afford a solution containing and 22 mg/2020 µl (~2.2% hydrogel) or 20.5 mg/2005 µl (2.05% hydrogel), respectively.

Results:

Hydrogel formation was observed within a few minutes. The formed hydrogels exhibit homogenous and transparent appearance, with a higher rigidity than the regular chitosan solution. Hydrogels containing the higher Fmoc-FF concentration were observed as having higher mechanical strength and more brittleness. Under a centrifugation process (10000 rpm for 20 seconds), no segregation or phase separation occurred in any of the formed hydrogels, indicating the stable nature of the hydrogel network.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A hydrogel comprising a fibrous network of a plurality of peptides and at least one biocompatible polymer, wherein said peptides are capable of self-assembling in an aqueous solution so as to form a hydrogel, and wherein each of said peptides independently comprises an aromatic amino acid, and wherein said biocompatible polymer is hyaluronic acid, the hydrogel being a hybrid hydrogel devoid of a chemical cross-linking agent.

2. The hydrogel of claim 1, wherein said biocompatible polymer features at least one characteristic selected from the group consisting of:
   (i) a storage, modulus G' lower than 500 Pa at 10 Hz frequency and at 25° C.;
   (ii) a swelling ratio (Q) higher than 500;
   (iii) a viscosity at 0.1 $Sec^{-1}$ shear rate and at 25° C., lower than 300 Pa·s; and
   (iv) a viscosity recovery shear of at least 95%.

3. The hydrogel of claim 1, wherein each peptide in said plurality of peptides independently comprises from up to six amino acid residues.

4. The hydrogel of claim 1, wherein each of said dipeptides is a dipeptide.

5. The hydrogel of claim 1, wherein each peptide in said plurality of peptides is an end-capping modified peptide.

6. The hydrogel of claim 5, wherein said end capping modified peptide comprises at least one end capping moiety, said end capping moiety being selected from the group consisting of an aromatic end capping moiety and a non-aromatic end-capping moiety.

7. The hydrogel of claim 6, wherein said aromatic end capping moiety is 9-fluorenylmethyloxycarbonyl (Fmoc).

8. The hydrogel of claim 1, wherein a total concentration of said plurality of peptides and said polymer ranges from 0.1 weight percent to 5 weight percents of the total weight of the gel.

9. The hydrogel of claim 1, wherein a weight ratio of said plurality of peptides and said polymer ranges from 10:1 to 1:10.

10. The hydrogel of claim 1, characterized by at least one of:
   a storage modulus G' to loss modulus G" ratio that is greater than 4;
   a storage modulus G' higher than 1,000 Pa at 10 Hz frequency and at 25° C.; and
   a storage modulus G' lower than 100,000 Pa at 10 Hz frequency and at 25° C.

11. The hydrogel of claim 1, characterized by:
   a viscosity that ranges from 200 to 2000 Pa·s at 0.1 $Sec^{-1}$ shear rate, at 25° C.;
   a viscosity recovery after shear of at least 50%, at 0.1 $sec^{-1}$; and
   a swelling ratio (Q) that ranges from 100 to 500.

12. A composition-of-matter comprising the hydrogel of claim 1 and at least one agent being incorporated therein or thereon.

13. A process of preparing the hydrogel of claim 1, the process comprising contacting said plurality of peptides and said biocompatible polymer in an aqueous solution.

14. A pharmaceutical, cosmetic or cosmeceutical composition comprising the hydrogel of claim 1.

15. A pharmaceutical, cosmetic or cosmeceutical composition comprising the composition-of-matter of claim 12.

16. An article-of-manufacture comprising the hydrogel of claim 1.

17. An article-of-manufacture comprising the composition-of-matter of claim 12.

18. A kit for forming the hydrogel of claim 1, the kit comprising said plurality of peptides and said biocompatible polymer.

19. The kit of claim 18, further comprising an aqueous solution, wherein said peptides and said aqueous solution are individually packaged within the kit.

20. A kit of for forming the composition-of-matter of claim 12, the kit comprising said plurality of peptides, said biocompatible polymer and said active agent.

21. The kit of claim 20, further comprising an aqueous solution, wherein said plurality of peptides and said aqueous solution are individually packaged within the kit.

22. A method of repairing a damaged tissue, the method comprising contacting the damaged tissue with the hydrogel of claim 1.

23. A method of repairing a damaged tissue, the method comprising contacting the damaged tissue with the composition-of-matter of claim 12.

* * * * *